United States Patent
Bertagnoli et al.

(10) Patent No.: US 7,547,308 B2
(45) Date of Patent: Jun. 16, 2009

(54) INSTRUMENTATION AND METHODS FOR PREPARATION OF AN INTERVERTEBRAL SPACE

(75) Inventors: Rudolf Bertagnoli, Vienna (AT); Tai Friesem, Ingleby Barwick (GB); Jean-Charles LeHuec, Pessac (FR); Hallett H. Mathews, Richmond, VA (US); Lukas Eisermann, Memphis, TN (US); Mingyan Liu, Bourg-la-Reine (FR); Loic Josse, Palaja (FR); Jeffrey Zhang, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 681 days.

(21) Appl. No.: 10/768,354

(22) Filed: Jan. 30, 2004

(65) Prior Publication Data
US 2005/0113842 A1    May 26, 2005

Related U.S. Application Data

(63) Continuation of application No. 10/430,473, filed on May 6, 2003, now abandoned, and a continuation of application No. PCT/US03/14170, filed on May 6, 2003.

(60) Provisional application No. 60/378,568, filed on May 6, 2002.

(51) Int. Cl.
*A61B 17/58* (2006.01)
(52) U.S. Cl. ...................................................... 606/90
(58) Field of Classification Search ................... 606/90, 606/99; 623/17.11–17.16
See application file for complete search history.

(56) References Cited

U.S. PATENT DOCUMENTS

| | | | | |
|---|---|---|---|---|
| RE20,389 | E | * | 6/1937 | Pickett .................... 600/238 |
| 2,483,997 | A | * | 10/1949 | Gjertsen .................. 451/477 |
| 4,299,347 | A | * | 11/1981 | Rougier .................... 225/97 |
| 4,697,586 | A | | 10/1987 | Gazale |
| 4,898,161 | A | | 2/1990 | Grundei |
| 5,122,130 | A | | 6/1992 | Keller |
| 5,135,528 | A | | 8/1992 | Winston |
| 5,431,658 | A | * | 7/1995 | Moskovich ................ 606/99 |
| 5,722,977 | A | | 3/1998 | Wilhelmy |
| 5,893,890 | A | * | 4/1999 | Pisharodi .............. 623/17.16 |
| 6,017,342 | A | * | 1/2000 | Rinner ..................... 606/57 |
| 6,190,414 | B1 | * | 2/2001 | Young et al. .......... 623/17.15 |
| 6,224,607 | B1 | | 5/2001 | Michelson |
| 6,241,729 | B1 | * | 6/2001 | Estes et al. ................ 606/61 |
| 6,261,296 | B1 | | 7/2001 | Aebi et al. |
| 6,267,354 | B1 | * | 7/2001 | Stephen ................. 254/93 R |
| 6,440,139 | B2 | | 8/2002 | Michelson |

(Continued)

FOREIGN PATENT DOCUMENTS

DE        295 20 928 U1    6/1996

(Continued)

*Primary Examiner*—Eduardo C Robert
*Assistant Examiner*—Nicholas Woodall

(57) ABSTRACT

An instrument for separating adjacent vertebrae includes a handle assembly and a distal portion at a distal end of the handle assembly. The distal portion includes first and second members movable from an unexpanded configuration for insertion in the disc space toward an expanded configuration to separate the vertebrae. A cutting member of a cutting instrument can be guided by the instrument to prepare the vertebrae for engagement with an implant.

44 Claims, 23 Drawing Sheets

U.S. PATENT DOCUMENTS

| | | | |
|---|---|---|---|
| 6,478,800 B1 | 11/2002 | Fraser et al. | |
| 6,565,574 B2 | 5/2003 | Michelson | |
| 6,652,533 B2 * | 11/2003 | O'Neil | 606/100 |
| 6,669,699 B2 * | 12/2003 | Ralph et al. | 606/61 |
| 6,692,501 B2 | 2/2004 | Michelson | |
| 6,761,723 B2 | 7/2004 | Buttermann et al. | |
| 6,770,074 B2 | 8/2004 | Michelson | |
| 6,814,738 B2 * | 11/2004 | Naughton et al. | 606/100 |
| 6,991,654 B2 * | 1/2006 | Foley | 623/17.16 |
| 7,169,152 B2 * | 1/2007 | Foley et al. | 606/90 |
| 2001/0031967 A1 | 10/2001 | Nicholson et al. | |
| 2002/0116009 A1 * | 8/2002 | Fraser et al. | 606/99 |
| 2004/0215198 A1 | 10/2004 | Marnay et al. | |
| 2004/0220582 A1 | 11/2004 | Keller | |
| 2006/0030856 A1 * | 2/2006 | Drewry et al. | 606/90 |

FOREIGN PATENT DOCUMENTS

| | | |
|---|---|---|
| DE | 200 05 812 U1 | 11/2000 |
| EP | 0 676 176 A1 | 10/1995 |
| EP | 0 681 811 A2 | 11/1995 |
| EP | 1 153 582 A2 | 11/2001 |
| EP | 122 903 A1 | 7/2002 |
| WO | WO 9847809 A1 * | 10/1998 |

* cited by examiner

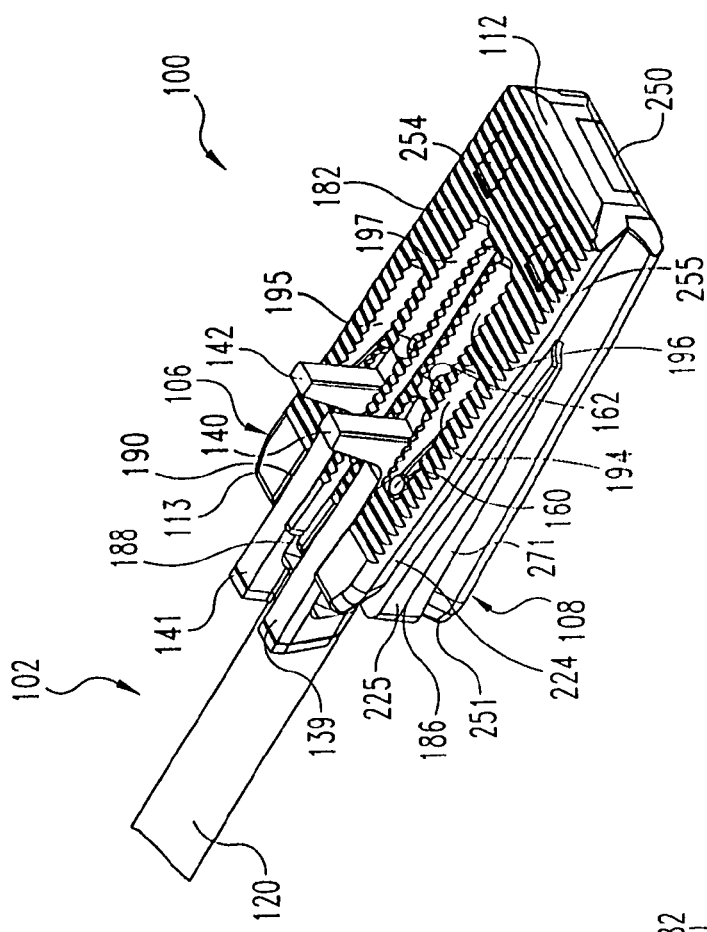
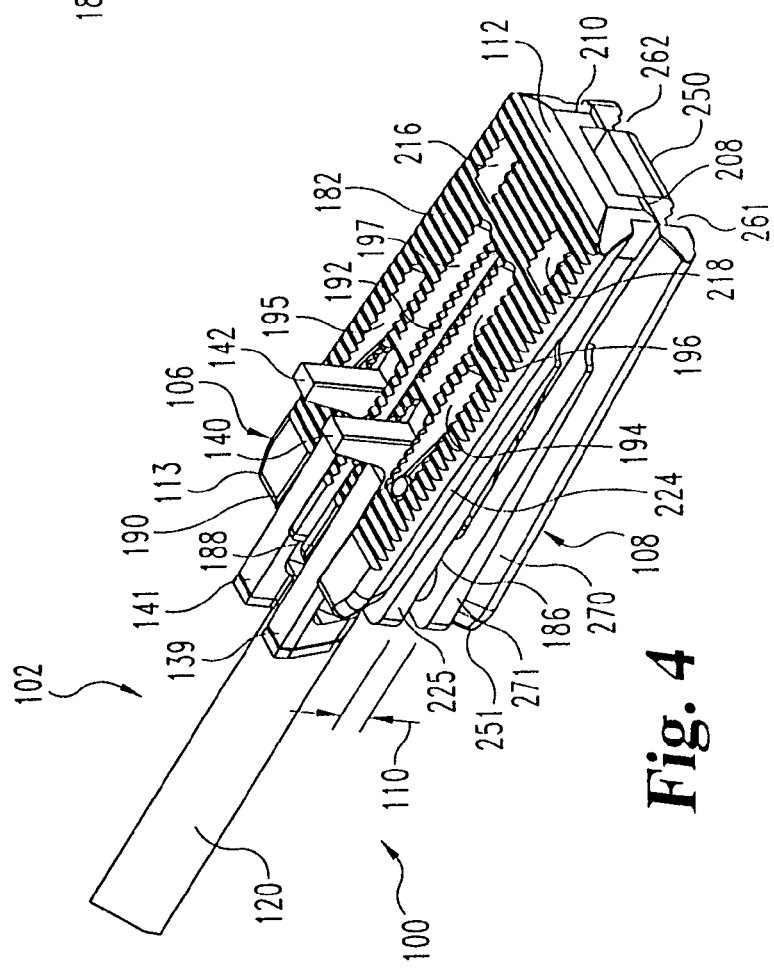

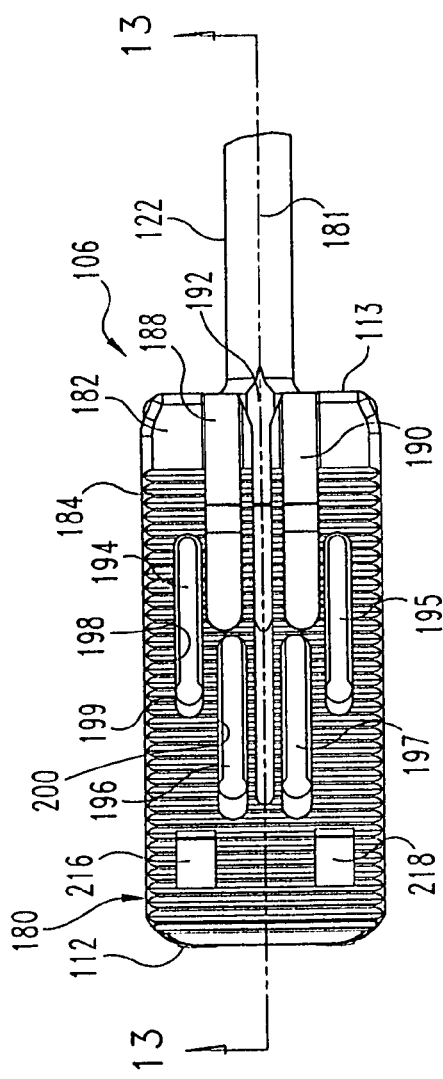
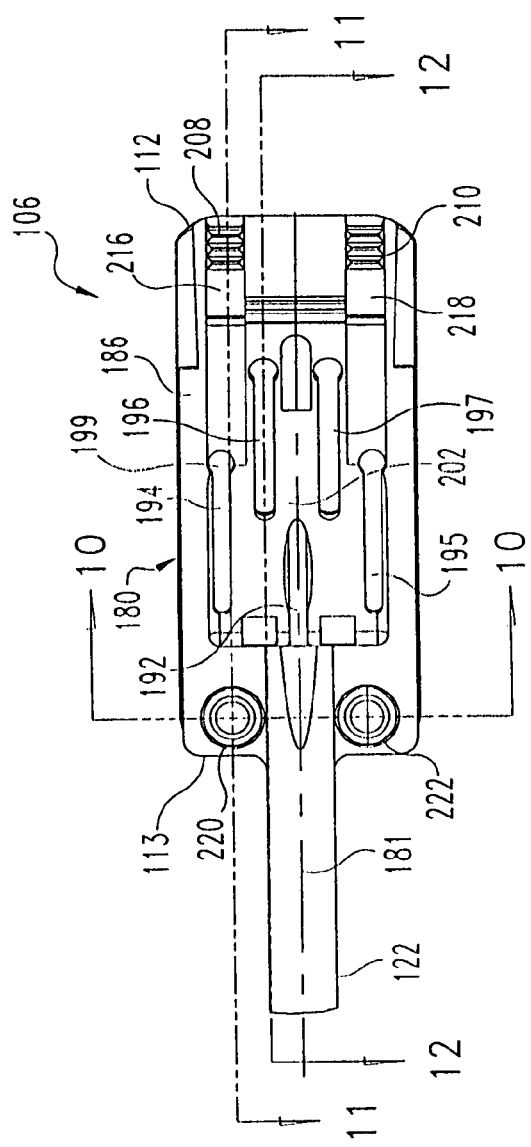

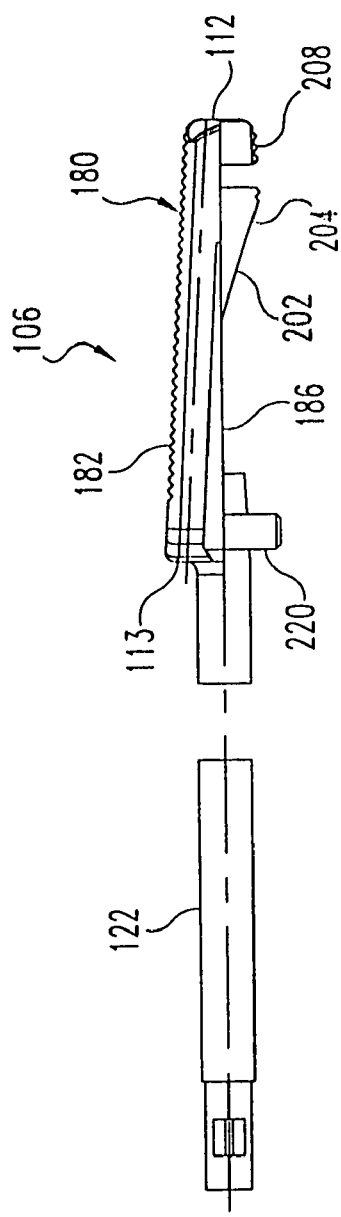
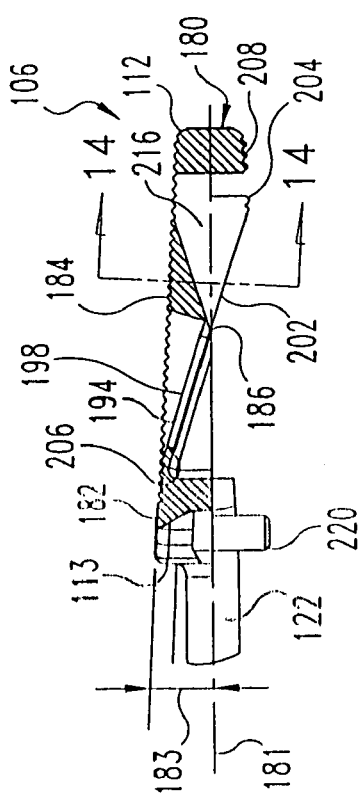
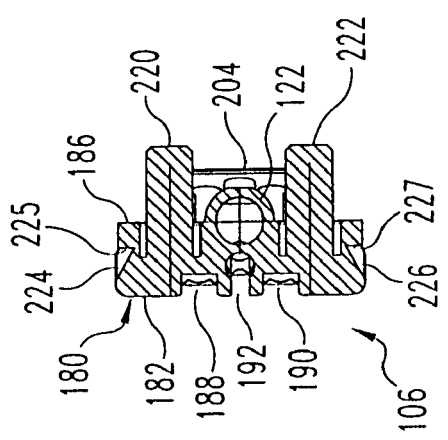
Fig. 9
Fig. 10
Fig. 11

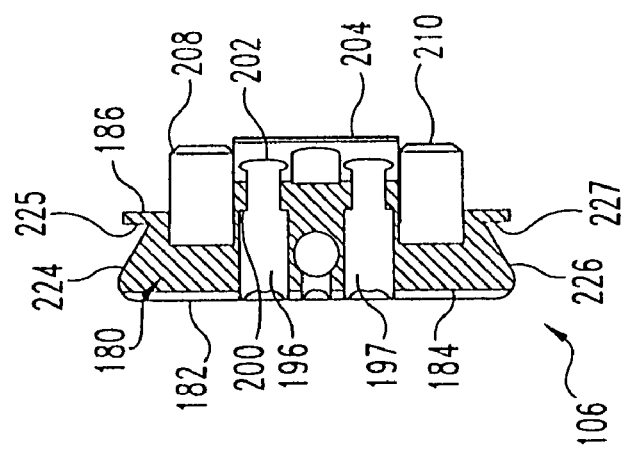
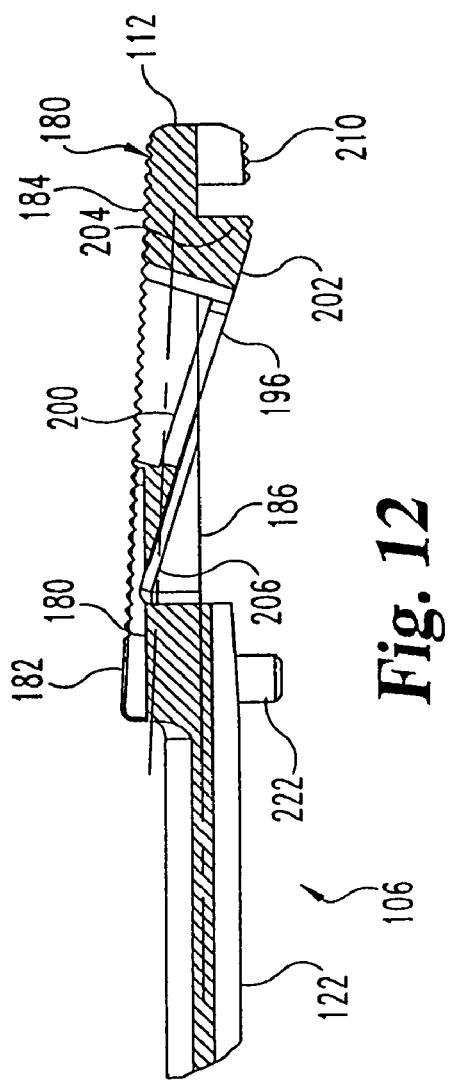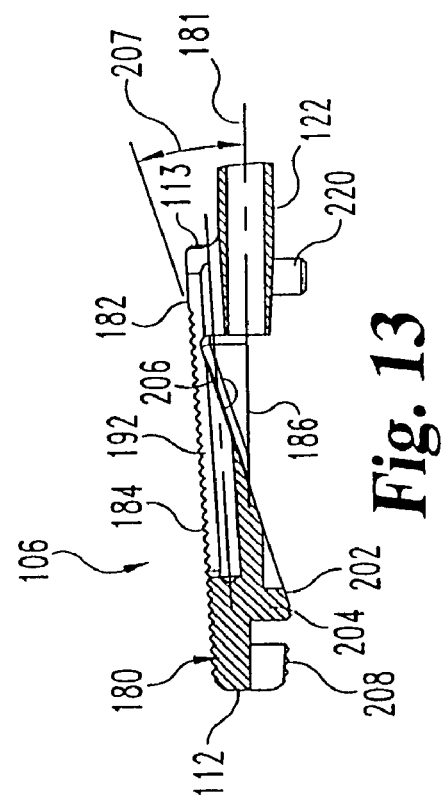

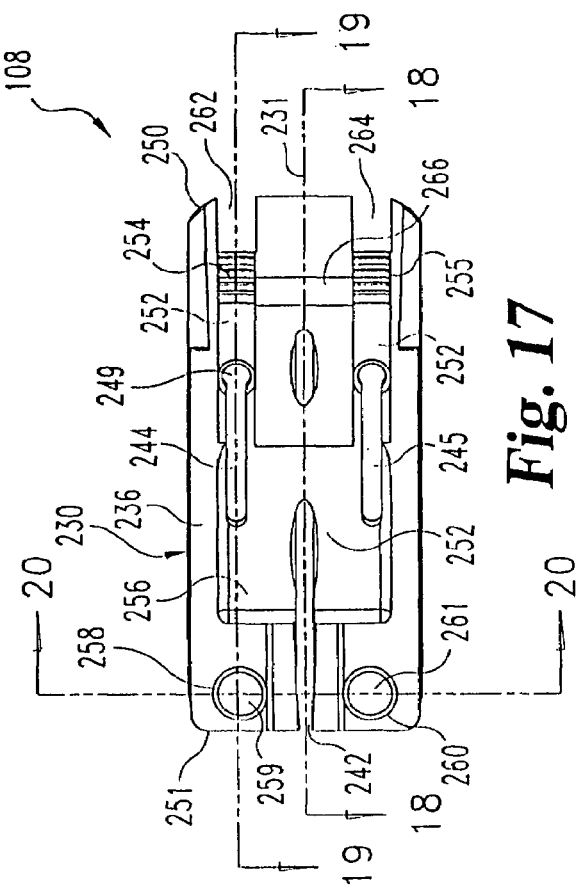
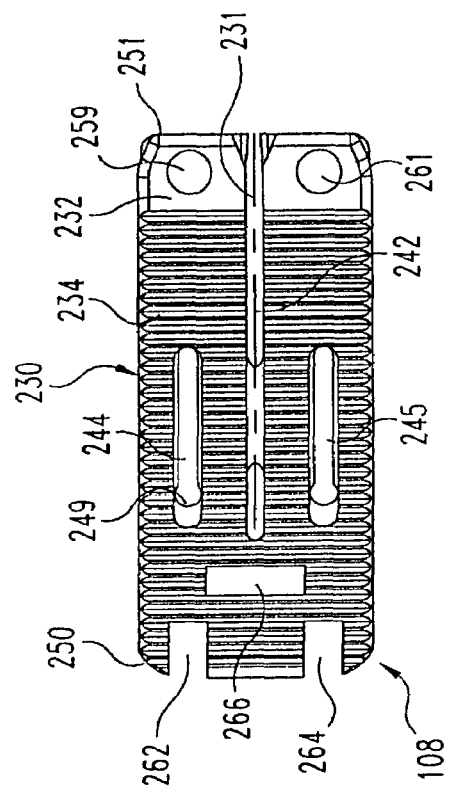
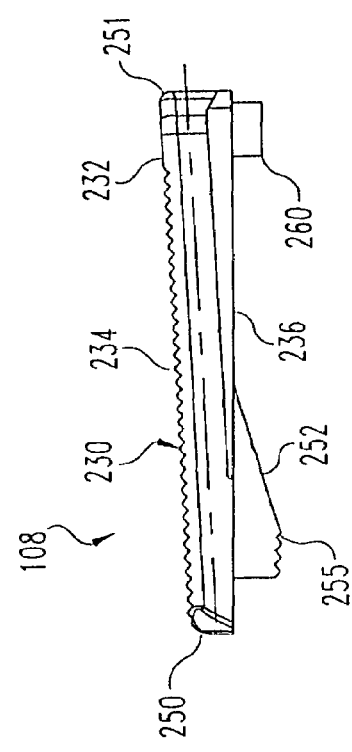

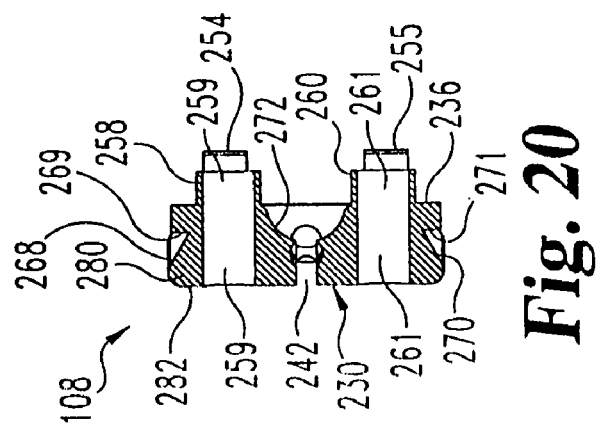
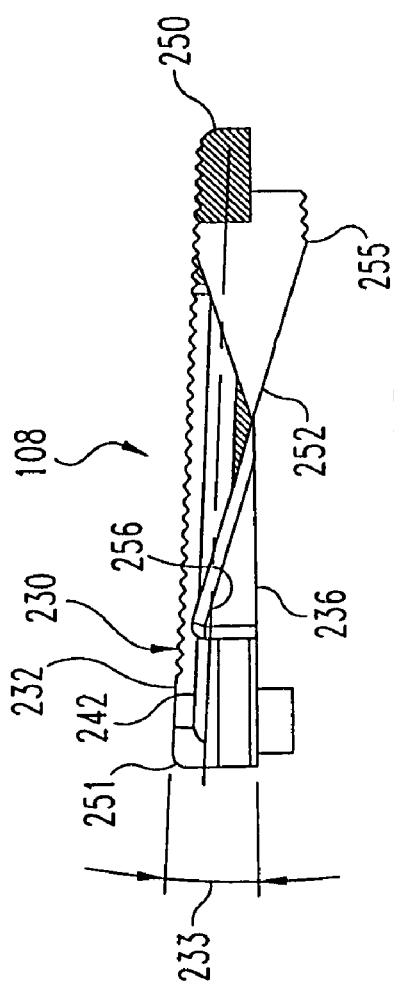
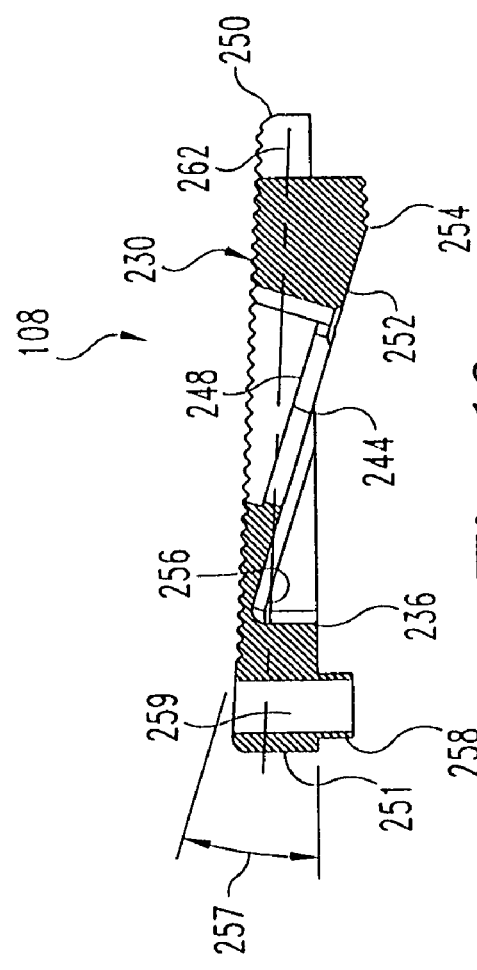

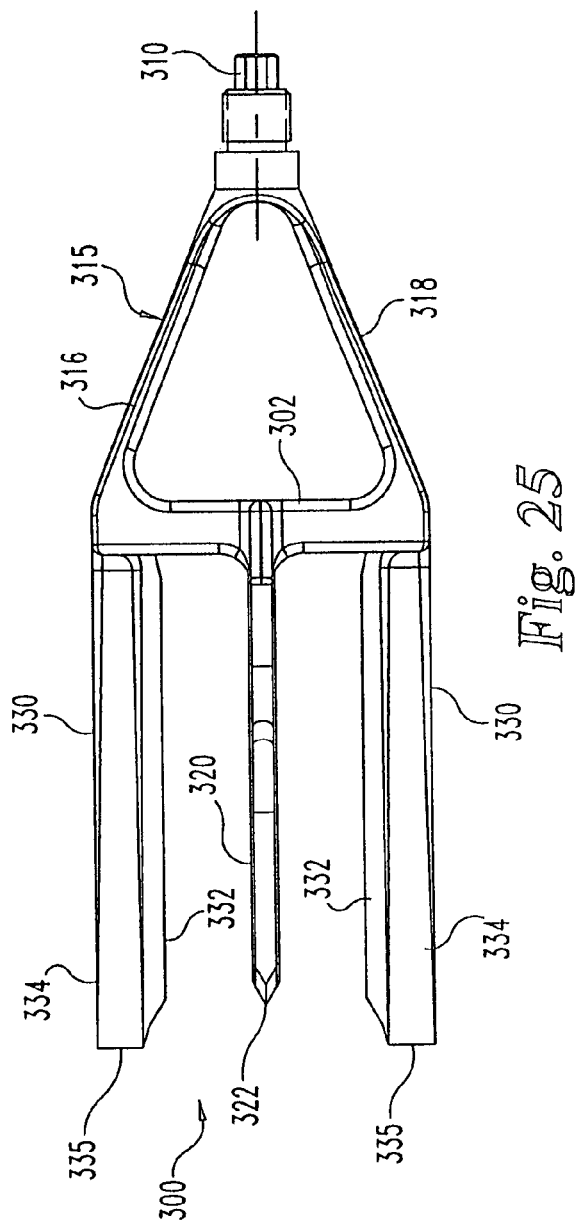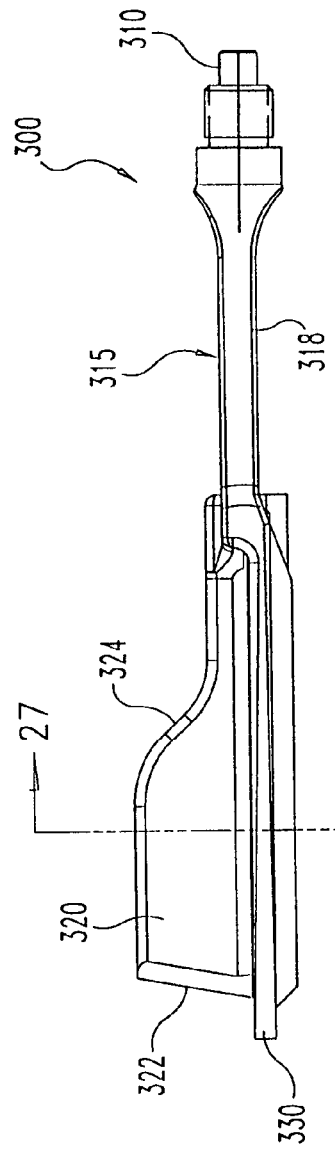

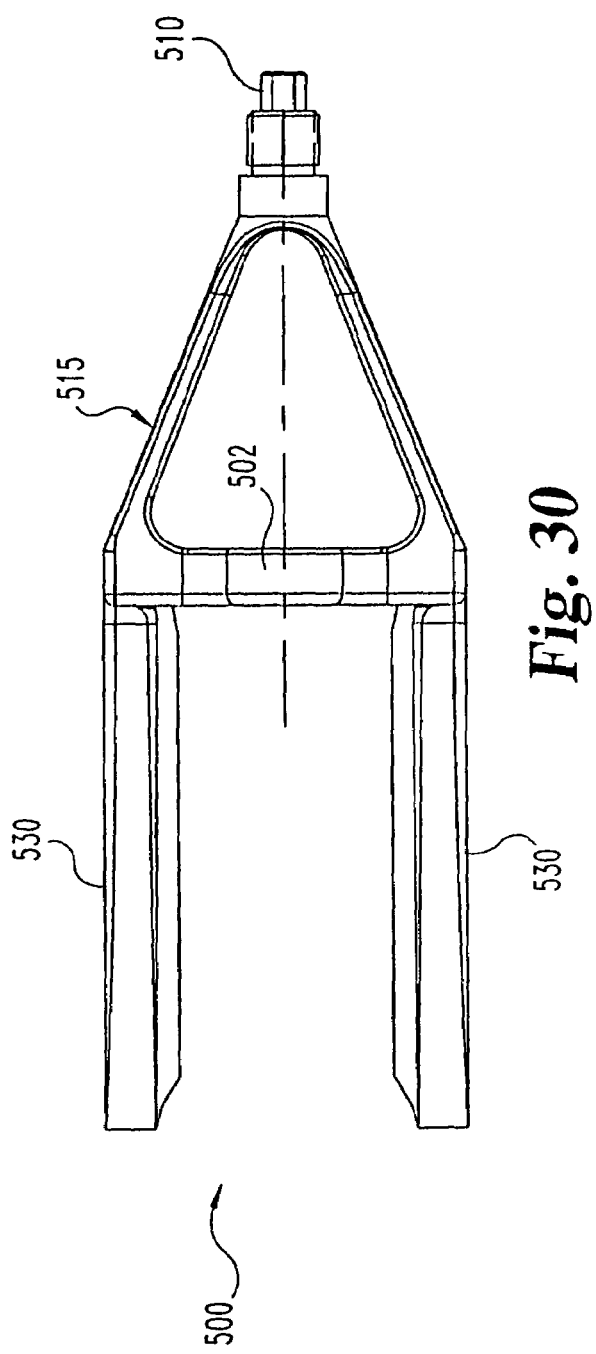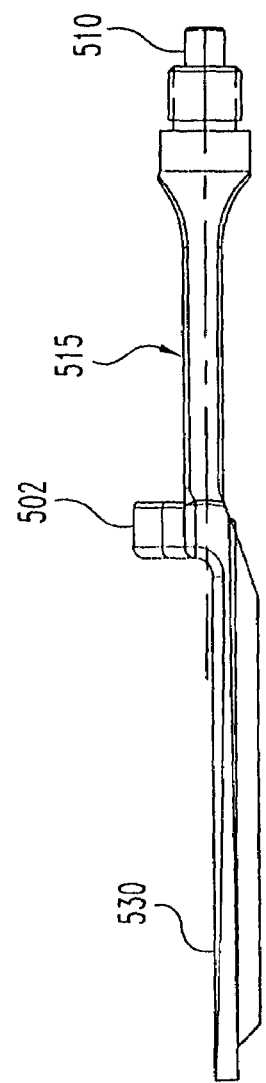

INSTRUMENTATION AND METHODS FOR PREPARATION OF AN INTERVERTEBRAL SPACE

CROSS-REFERENCE TO RELATED APPLICATION

This application is a continuation of U.S. patent application Ser. No. 10/430,473 filed May 6, 2003, now abandoned, which claims the benefit of the filing date of U.S. Provisional Application Ser. No. 60/378,568 filed on May 6, 2002, now expired. This application is also a continuation of PCT Application No. PCT/US03/14170 filed on May 6, 2003, which claims priority to U.S. Provisional Application Ser. No. 60/378,568 filed on May 6, 2002, now expired. Each of the referenced applications is incorporated herein by reference in its entirety.

BACKGROUND

Restoration and preparation of the space between vertebrae and preparation of the vertebral bodies can be important to obtain the desired fit of implants and other devices in the disc space and with the vertebral bodies. There remains a need for instruments and techniques that facilitate such restoration of the space between vertebrae and the preparation of the vertebrae to receive or engage implants.

SUMMARY

According to one aspect, there is provided an instrument for separating adjacent vertebrae that includes a handle assembly and a distal portion at a distal end of the handle assembly. The distal portion includes first and second members movable from an unexpanded configuration for insertion in the disc space toward an expanded configuration to separate the vertebrae.

According to another aspect, there is provided an instrument for separating adjacent vertebrae and a cutting member of a cutting instrument guided by the instrument to prepare the vertebrae for engagement with an implant.

According to a further aspect, there is provided an instrument for separating adjacent vertebrae that includes a handle assembly and a distal portion at a distal end of the handle assembly. The distal portion includes at least one actuating member movably positioned between first and second members.

These and other aspects are discussed below.

BRIEF DESCRIPTION OF THE DRAWINGS

FIG. 3 is a perspective of the distal portion of FIG. 2 in an unexpanded configuration and rotated 180 degrees about the longitudinal axis of the instrument from its FIG. 2 orientation.

FIG. 4 is a perspective of the distal portion of FIG. 2 in an expanded configuration and rotated 180 degrees about the longitudinal axis of the instrument from its FIG. 2 orientation.

FIG. 7 is a top plan view of the distal portion of the instrument portion of FIG. 5.

FIG. 8 is a bottom plan view of the distal portion of the instrument portion of FIG. 5.

FIG. 9 is an elevation view of the distal portion of the instrument portion of FIG. 5.

FIG. 10 is a section view through line 10-10 of FIG. 8.

FIG. 11 is a partial section view through line 11-11 of FIG. 8.

FIG. 12 is a section view through line 12-12 of FIG. 8.

FIG. 13 is a section view through line 13-13 of FIG. 7.

FIG. 14 is a section view through line 14-14 of FIG. 11.

FIG. 15 is a top plan view of the second member comprising a part of the distal portion of the instrument of FIG. 1.

FIG. 16 is a side elevation view of the second member of FIG. 17.

FIG. 17 is a bottom plan view of the second member of FIG. 17.

FIG. 18 is a section view through line 18-18 of FIG. 17.

FIG. 18A is a section view through line 18-18 of FIG. 17 of another second member.

FIG. 19 is a section view through line 19-19 of FIG. 17.

FIG. 20 is a section view through line 20-20 of FIG. 17.

FIG. 25 is a plan view of the combination chisel of FIG. 24.

FIG. 26 is a side elevation view of the combination chisel of FIG. 24.

FIG. 30 is a plan view of a corner chisel.

FIG. 31 is an elevation view of the corner chisel of FIG. 30.

DESCRIPTION OF THE ILLUSTRATED EMBODIMENTS

Figure 1:
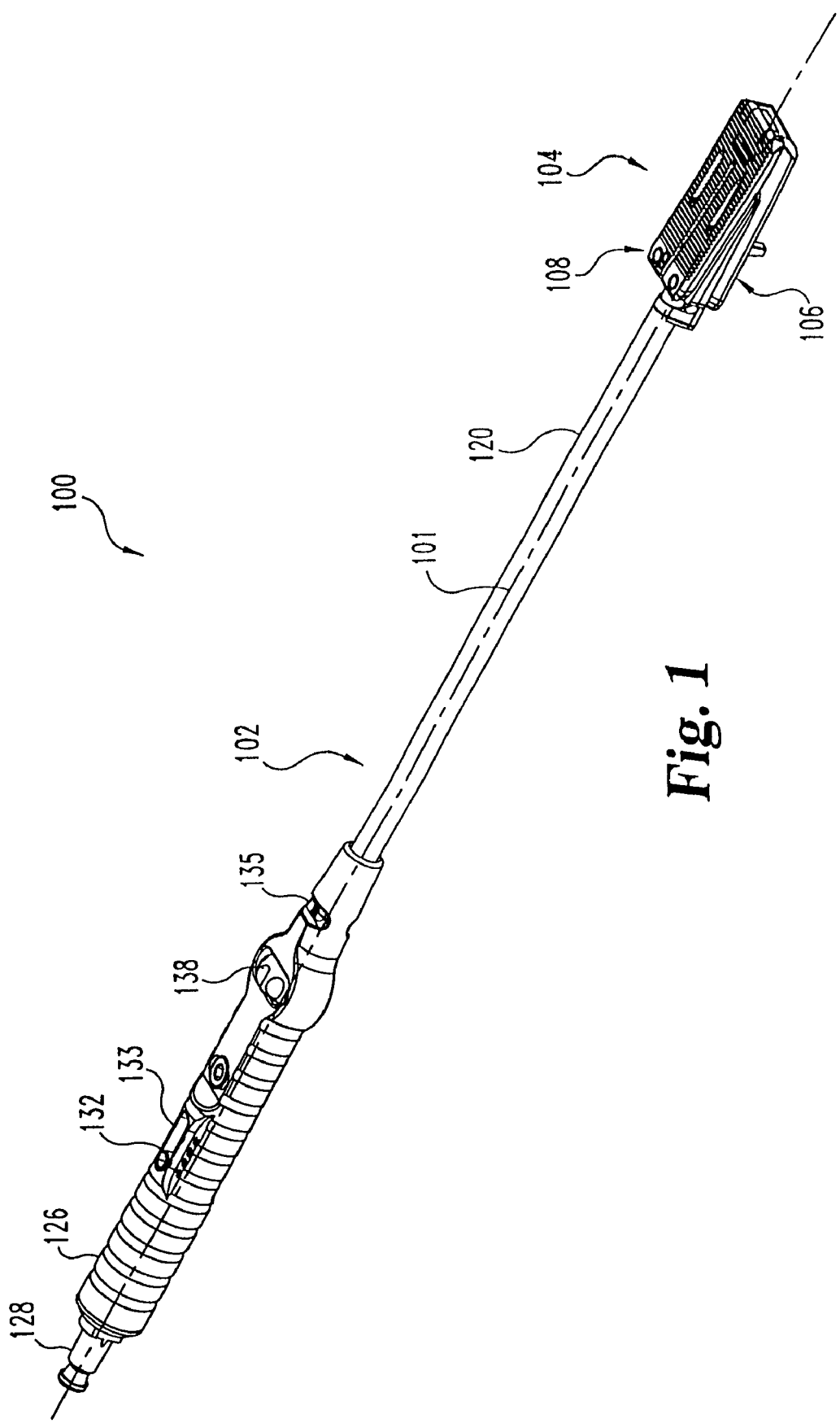
FIG. 1 is a side perspective view of an instrument for distracting and facilitating preparation of an intervertebral space according to one form of the present invention.

For the purposes of promoting an understanding of the principles of the present invention, reference will now be made to the embodiments illustrated in the drawings and specific language will be used to describe the same. It will nevertheless be understood that no limitation on the scope of the present invention is intended, and any alterations or modifications in the disclosed embodiments and further applications of the principles of the present invention are contemplated as would normally occur to one skilled in the art to which the present invention relates.

Referring to FIG. 1, there is shown an instrument 100 having a handle assembly 102 extending along longitudinal axis 101. Instrument 100 includes a distal portion 104 at a distal end of handle assembly 102. Distal portion 104 is positionable in a space between vertebrae and can be remotely manipulated by the surgeon to increase the separation distance and/or angulation between the adjacent vertebrae. Distal portion 104 includes a first member 106 and a second member 108. In the illustrated embodiment, the members 106, 108 are in the form of plates having opposite faces positionable against the endplate of an adjacent vertebrae to provide a separation force thereto when manipulated with handle assembly 102. Other forms for members 106, 108 are also contemplated, including single blades, U-shaped blades, or other suitable structure for contacting the adjacent vertebral endplate.

Figure 2:
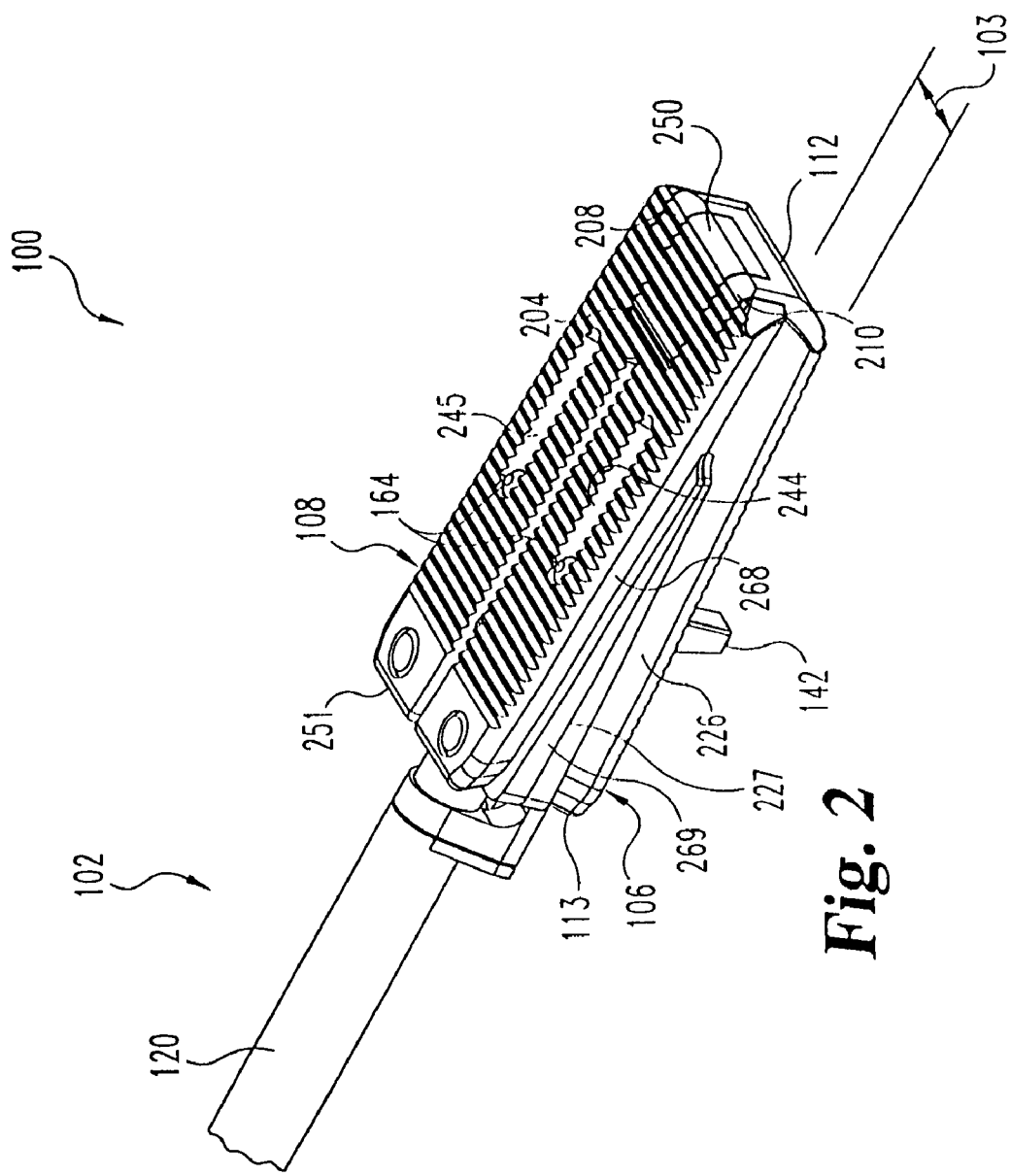
FIG. 2 is a perspective of a distal portion of the instrument of FIG. 1.

First and second members 106, 108 are movable relative to one another from an unexpanded configuration, as shown in FIGS. 1-3, to a second expanded configuration, as shown in FIG. 4. In the unexpanded configuration, first and second members 106, 108 are positioned adjacent one another to form a low profile configuration for insertion in the space between the vertebrae. In the expanded configuration, first member 106 and second member 108 are moved away from one another and separated by a distance 110. Distance 110 can be increased or decreased by manipulation of handle assembly 102 to provide a desired separation distance between adjacent vertebrae in contact with first and second members 106, 108.

Figure 5:
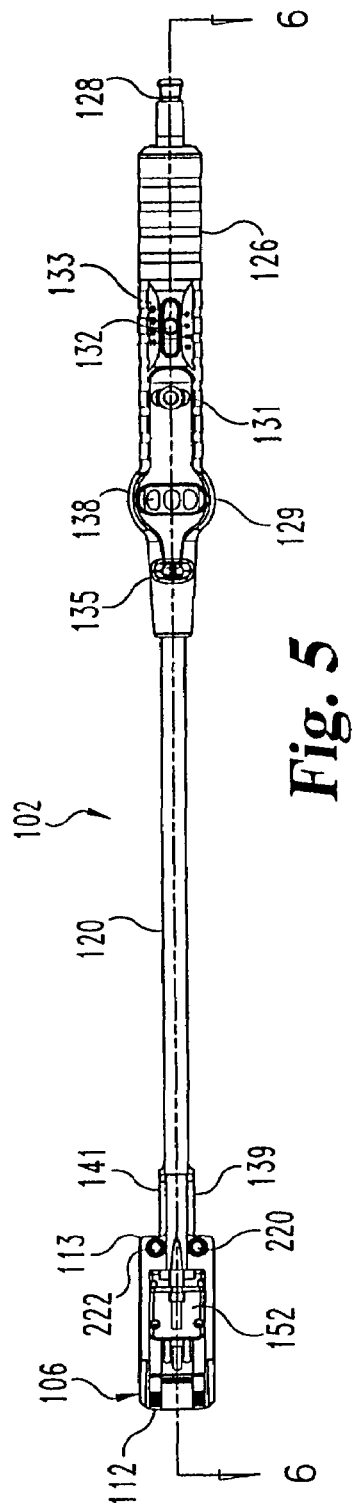
FIG. 5 is a bottom plan view of a portion of the instrument of FIG. 1 with a second member of the distal portion of the instrument removed therefrom.
Figure 6:
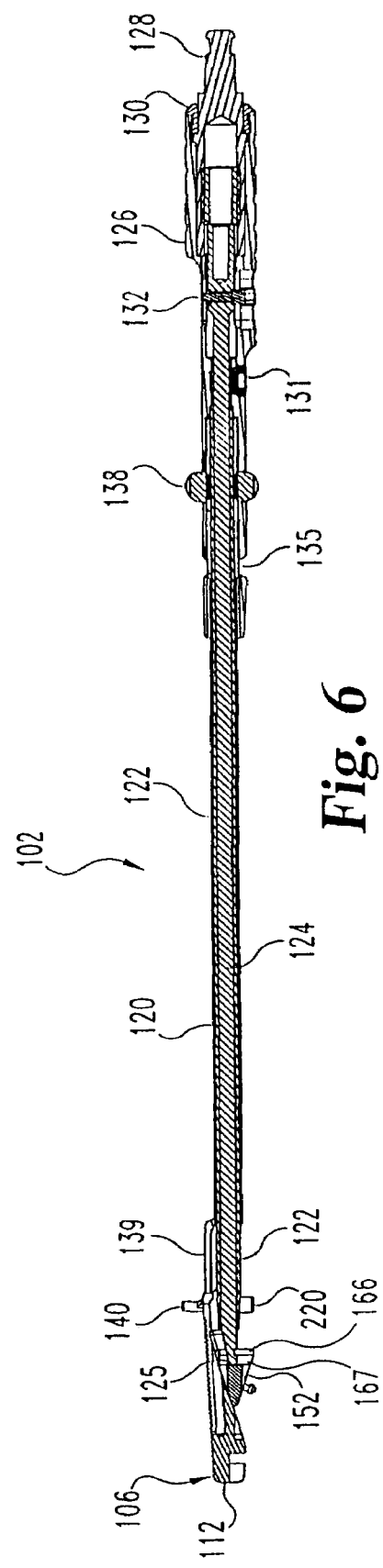
FIG. 6 is a section view through line 6-6 of FIG. 5.

Further details regarding handle assembly 102 will now be discussed with reference to FIGS. 5 and 6. First member 106 is coupled with an intermediate shaft 122 extending proximally therefrom. First member 106 can be integrally formed with intermediate shaft 122 or otherwise attached thereto. Intermediate shaft 122 is received in a passage formed through an outer shaft 120. Intermediate shaft 122 further includes a passage through which an inner shaft 124 extends. A handle member 126 extends proximally about the proximal ends of shafts 120, 122 and 124. Outer shaft 120 is movable relative to intermediate shaft 122 with thumbwheel 138. Thumbwheel 138 is rotatably received in enlarged portion 129 of handle member 126 and threadingly engaged with outer shaft 120 to provide axial adjustment capability for outer shaft 120 relative to intermediate shaft 122.

Outer shaft 120 includes first and second arms 139, 141 extending distally and longitudinally from a distal end thereof. First arm 139 includes a first stop member 140 at a distal end thereof, and second arm 141 includes a second stop member 142 at a distal end thereof. The distance from stop members 140, 142 to the distal end 112 of first member 106 is indicated by depth markings along outer shaft 120, which are visible through a window 135 formed in handle member 126. First and second stop members 140, 142 extend transversely to longitudinal axis 101 and project outwardly from first member 106. First and second stop members 140, 142 contact the adjacent vertebral body to limit the depth of insertion of distal portion 104 into the space between vertebrae. First and second stop members 140, 142 are adjustable relative to intermediate shaft 122 and first member 106 with thumbwheel 138 to allow the desired insertion depth limit into the disc space for distal portion 104 to be adjusted by the surgeon.

Inner shaft 124 includes an actuating member 152 coupled to a distal end thereof. Actuating member 152 is positioned between first member 106 and second member 108. Actuating member 152 is movable distally relative to first and second members 106, 108 with inner shaft 124 to move first and second members 106, 108 toward the expanded configuration. A distraction indicator 132 coupled to inner shaft 124 moves longitudinally therewith to provide an indication of the position of actuating member 152 relative to first and second members 106, 108. Distraction height indicia 133 on handle member 126 correspond to the distraction height of first and second members 106, 108 provided by the longitudinal positioning of actuating member 152 therebetween.

In the illustrated embodiment, inner shaft 124 is axially movable relative to intermediate shaft 122 and outer shaft 120 by coupling a T-handle (not shown) to connector 128. Connector 128 can be a Hudson type connector or any other suitable structure for engagement with the T-handle. Connector 128 extends into handle member 126 and is threadingly engaged with a proximal end of inner shaft 124. An end cap 130 centers connector 128 in the proximal end opening of handle member 126. Rotation of connector 128 in one of the clockwise or counter-clockwise directions results in distal axial movement of inner shaft 124 and actuating member 152, causing first and second members 106, 108 to move toward their expanded configuration. Rotation of connector 128 in the opposite direction results in proximal axial movement of inner shaft 124 and actuating member 152, allowing first and second members 106, 108 to return toward their unexpanded configuration.

Handle assembly 102 further includes a coupling member 131 extending about intermediate shaft 122 and keyed with the sides thereof to prevent intermediate shaft 122 from rotating with the rotation of inner shaft 124. Coupling member 131 further releasably secures handle member 126 to intermediate shaft 122. Coupling member 131 can be accessed and removed to allow disassembly of handle assembly 102 to facilitate cleaning of instrument 100.

Referring now to FIGS. 7-14, further details of first member 106 will be discussed. First member 106 includes a plate-like body 180 forming a distal extension of intermediate shaft 122. Body 180 extends between a distal end 112 and a proximal end 113. Body 180 includes an outer surface 182 having a number of V-shaped, elongated recesses 184 formed therein. Recesses 184 provide frictional engagement with the adjacent vertebral endplate, and resist movement of first member 106 relative to the vertebrae during the surgical procedure. Body 180 includes an inner surface 186 configured to co-act with actuating member 152 and second member 108 to couple first and second members 106, 108 to one another and to move between the expanded and unexpanded positions.

Body 180 extends along a central axis 181 and includes a central keyway 192 extending from proximal end 113 along axis 181 along a portion of the length of body 180. Keyway 192 opens along outer surface 182. Body 180 further includes grooves 188, 190 offset from and extending along axis 181 that open toward outer surface 182 and proximal end 113. Arms 139, 141 of outer shaft 120 are slidably received and recessed in respective ones of the grooves 188, 190. Body 180 further includes lateral actuator slots 194, 195 and medial actuator slots 196, 197 extending between and opening at each of the outer and inner surfaces 182, 186. Medial slots 196, 197 are offset distally relative to lateral slots 194, 195. Slot 194 includes an intermediate surface 198 oriented toward outer surface 182 that supports the enlarged head of an engagement member of the actuating member, as discussed further below. Slot 194 further includes an enlarged distal end 199 through which the enlarged head of a corresponding engagement member of the actuating member can be positioned to couple actuating member 152 thereto. Each of the slots 195, 196, 197 similarly include an intermediate surface and enlarged distal end for receiving a corresponding enlarged head of an engagement member of actuating member 152. For example, as shown in FIGS. 12 and 14, medial slot 196 includes an intermediate surface 200 for supporting the underside of the enlarged head of the corresponding engagement member of actuating member 152 as it moves therealong.

Inner surface 186 includes a cam surface 202 extending along axis 181. Cam surface 202 extends along a distal projection portion 204 adjacent distal end 112 and a proximal recessed portion 206 adjacent proximal end 113, as shown in FIGS. 11-13. Projection portion 204 projects downwardly toward second member 108 adjacent distal end 112, as best shown in FIGS. 9 and 11-13. Recessed portion 206 extends into body 180 adjacent proximal end 113, as best shown in FIGS. 11-13. Cam surface 202 forms angle 207 with central axis 181. In one embodiment, angle 207 is 17.5 degrees; however, other cam surface angles are also contemplated. The intermediate surfaces of slots 194, 195, 196, 197, such as intermediate surfaces 198, 200 shown in FIGS. 11 and 12, extend parallel to cam surface 202 to facilitate movement of actuating member 152 therealong.

First member 106 includes a first distal arm 208 and a second distal arm 210 on opposite sides of central axis 181. Distal arms 208, 210 project toward second member 108 adjacent distal end 112. A first passage 216 extends from inner surface 186 and opens at outer surface 182 along the proximal side of first distal arm 208, and a second passage 218 extends from inner surface 186 and opens at outer surface 182 along the proximal side of second distal arm 210. First member 106 further includes a first proximal post 220 and a second proximal post 222 on opposite sides of axis 181 that project from inner surface 186 adjacent proximal end 113 toward second member 108.

Referring now to FIGS. 15-20, further details of second member 108 will be discussed. Second member 108 includes a plate-like body 230 that is coupled to first member 106 with actuating member 152. Body 230 extends between a distal end 250 and a proximal end 251. Body 230 includes an outer surface 232 having a number of V-shaped grooves 234 formed therein. Grooves 234 provide frictional engagement with the adjacent vertebral endplate, and resist movement of second member 108 relative to the vertebrae during the surgical procedure. Body 230 includes an inner surface 236 configured to co-act with actuating member 152 to couple first and second members 106, 108 to one another during movement between the expanded and unexpanded configurations.

Body 230 extends along a central axis 231 and includes a central keyway 242 extending from proximal end 251 along axis 231 along a portion of the length of body 230. Keyway 242 opens along outer surface 232. Body 180 further includes actuator slots 244, 245 extending between and opening toward each of the outer and inner surfaces 232, 236. Slot 244 includes an intermediate surface 248 oriented toward outer surface 232 that supports the head of an engagement member of the actuating member, as discussed further below. Slot 244 further includes an enlarged distal end 249 through which the head of the engagement member of the actuating member is positioned to couple the actuating member 152 thereto. Slot 245 similarly includes an intermediate surface and enlarged distal end for receiving a corresponding engagement member of the actuating member 152.

Inner surface 236 includes a cam surface 252 extending along axis 181. Cam surface 252 extends along distal projection portions 254, 255 adjacent distal end 250 and a proximal recess portion 256 adjacent proximal end 251, as shown in FIG. 20. Projection portions 254, 255 project toward first member 106, as shown in FIGS. 16 and 18-19. Recess portion 256 extends into body 230 adjacent proximal end 251, as best shown in FIGS. 18-19. Cam surface 252 forms angle 257 with central axis 231. In one embodiment, angle 257 is the same as cam surface angle 207 of first member 106 and is 17.5 degrees; however, other cam surface angles are also contemplated. The intermediate surfaces of slots 244, 245, such as intermediate surface 248 shown in FIG. 19, extends parallel to cam surface 252 to facilitate movement of actuating member 152 therealong.

Second member 108 includes a first proximal receiving member 258 and a second proximal receiving member 260 on opposite sides of central axis 231. Receiving members 258, 260 project toward first member 106. Receiving member 258 includes a passage 259 extending therethrough and opening at outer surface 232, and receiving member 260 includes a passage 261 extending therethrough and opening at outer surface 232. Second member 108 further includes a first distal notch 262 and a second distal notch 264 each opening toward distal end 250. A central receptacle 266 opens toward outer surface 232 and inner surface 236, and is located distally of central keyway 242. Shaft receptacle 272 is positioned between receiving members 258, 260 to receive the distal end of intermediate shaft 122 in the unexpanded configuration.

Figure 22:
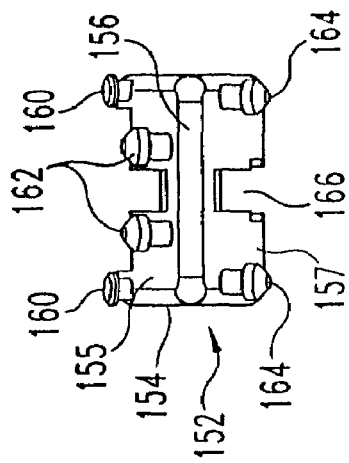
FIG. 22 is an elevation view of the actuating member of FIG. 21.
Figure 23:
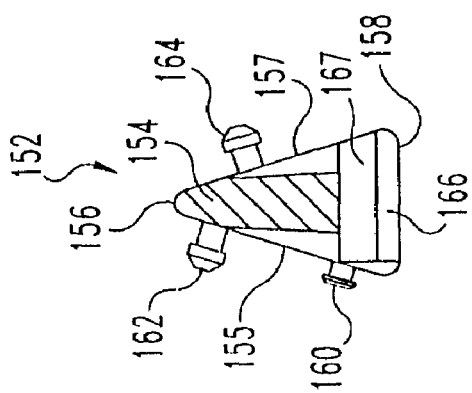
FIG. 23 is a section view through line 23-23 of FIG. 21.
Figure 21:
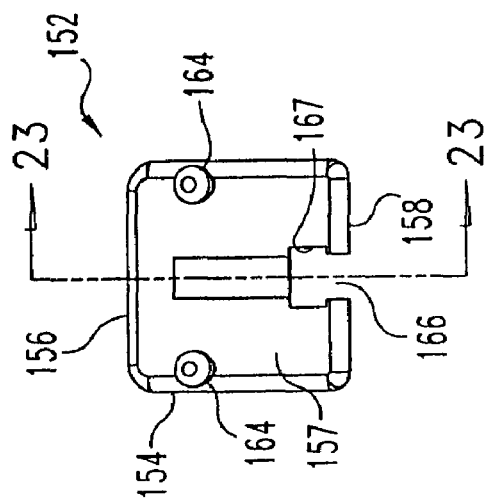
FIG. 21 is a plan view of an actuating member comprising a portion of the instrument of FIG. 1.

Referring now to FIGS. 21-23, further details of actuating member 152 are provided. Actuating member 152 includes a wedge-shaped body 154 having a first surface 155 and an opposite second surface 157. Surfaces 155, 157 taper toward one another from proximal end 158 to distal end 156 when actuating member 152 is positioned between first and second members 106, 108. Accordingly, proximal end 158 has a thickness greater than that of distal end 156.

A pair of distal engagement members 162 extend from first surface 155 adjacent distal end 156, and a pair of proximal engagement members 160 extend from first surface 155 adjacent proximal end 158. Proximal engagement members 160 are slidably received within respective ones of the lateral slots 194, 195 of first member 106, and distal engagement members 162 are slidably received within respective ones of the medial slots 196, 197 of first member 106. A pair of opposite engagement members 164 extend from second surface 157 and are slidingly received within respective ones of the actuator slots 244, 245 of second member 108. Each of the engagement members 160, 162, 164 includes an enlarged head portion positionable through the enlarged distal end opening of the corresponding slot, and engages intermediate surface of the corresponding slot when moved proximally from the enlarged distal opening. Engagement of actuator 152 within the slots couples second member 108 to first member 106.

Actuating member 152 further includes a proximally opening notch 166 extending along proximal end 158 toward distal end 156 along a portion of first and second surface 155, 157. Inner shaft 124 includes a flanged distal end 125 slidably coupled to actuating member 152 in grooved portion 167 of notch 166, as shown in FIG. 6. It is contemplated that actuator 152 moves up and down along flanged distal end 125 of inner shaft 124 as actuating member is moved along the cam surfaces of first and second members 106, 108.

When distal portion 104 is assembled, actuating member 152 is located between and movably coupled to first and second members 106, 108. Proximal engagement members 160 are slidably received in respective ones of the lateral actuator slots 194, 195 of first member 106, and distal engagement members 162 are slidably received in medial actuator slots 196, 197 of first member 106. Similarly, engagement members 164 are slidably received in actuator slots 244, 245 of second member 108. The enlarged heads of engagement members 160, 162, 164 extend along the intermediates surfaces of the actuator slots to secure the first and second members 106, 108 to actuating member 152.

Surface 155 of actuating member 152 contacts cam surface 202 of first member 106, and surface 157 of actuating member 152 contacts cam surface 252 of second member 108. Surfaces 155, 157 are angled relative to one another to match the cam surface angles 207, 257 formed by cam surfaces 202, 252. In the unexpanded condition, actuating member 152 is located in recessed portions 206, 256 so that inner surfaces 186, 206 are positioned adjacent to one another. In the expanded condition, actuating member 152 is moved distally along cam surfaces 202, 252 along the respective distal projection portion 204 of first member 206 and distal projection portions 254, 255 of second member 208. This distal movement of actuating member 152 moves first and second members 106, 108 away from one another toward the expanded configuration. Actuating member 152 acts on cam surfaces 202, 252 so that the distal ends 112, 250 are moved away from one another the same distance that proximal ends 113, 251 are moved away from one another.

Other embodiments contemplate other movement of actuating member 152 relative to first and second members 106, 108 to provide an expanded configuration. For example, actuating member 152 can be configured so that its rotation about the longitudinal axis of instrument 100 moves first and second members 106, 108 toward the expanded configuration. In another form, actuating member 152 can be rotated about the longitudinal axis of the instrument and simultaneously moved along the longitudinal axis of the instrument to move first and second members 106, 108 toward the expanded configuration.

To provide lateral stability and a low profile for distal portion 104 for insertion in the space between vertebrae, the projections and recesses of the first and second members 106, 108 are received in interfitting recesses and projections of the other of the first and second members. When first and second members 106, 108 are assembled, distal projection portion 204 of first member 106 is aligned with and received in central receptacle 266 of second member 108, and distal arms 208, 210 of first member 106 are aligned with and received in distal notches 264, 262 of second member 108. Proximal posts 220, 222 of first member 106 are aligned with and received in the passages of the corresponding proximal receiving member 260, 258 of second member 108. Distal projection portions 254, 255 of second member 108 are aligned with and received in respective ones of the first and second passages 216, 218 of first member 106 in the unexpanded configuration.

When assembled, the first and second members 106, 108 define a pair of opposed outer surfaces 182, 232. The outer surfaces 182, 232 are sized to be inserted into an intervertebral disc space and are adapted to contact and securely engage opposing faces of the adjacent vertebrae. In one embodiment, outer surfaces 182, 232 define a number of surface features that aid in engaging and gripping the vertebral endplates of the adjacent vertebrae, such as recesses 184, 234. In a specific embodiment, recesses 184, 234 are V-shaped and arranged at approximately a 45° angle across the respective outer surface 182, 232 and extend orthogonally to longitudinal axis 101.

The outer surfaces 182, 232 are generally planar and are of uniform relative separation across their widths in a direction transverse to longitudinal axis 101 such that a cross section of the first and second members 106, 108 perpendicular to the longitudinal axis 101 is generally rectangular. Other cross sectional profiles including profiles that vary along the longitudinal axis 101 could also be employed.

Outer surfaces 182, 232 can be tapered relative to one another and oriented to form an angle 103 such that the degree of angular separation between the outer surfaces 132, 182 decreases towards the distal ends 112, 250 of first and second members 106, 108. The angle 103 defined between outer surfaces 182, 232 can correspond to the particular lordotic angle desired between the endplates of the vertebrae on each side of the intervertebral disc space, and may take on any number of specific values, including 6°, 9°, and 12°, for example. It should be understood, however, that other angles 103 are contemplated, including angles at or near 0° where outer surfaces 182, 232 are arranged substantially parallel to one another. Still other embodiments contemplate variable or kyphotic angles between the outer surfaces 182, 232.

In one specific embodiment, first member 106 includes outer surface 182 that is oriented at angle 183 relative to central axis 181, as shown in FIG. 11. As shown in FIG. 18, second member 108 includes an outer surface 232 oriented at an angle 233 relative to a plane that extends parallel to axis 181 when first and second members 106, 108 are assembled. Accordingly, overall angle 103 is equal to the sum of angles 183 and 233 when first and second members 106, 108 are assembled. Providing first and second members 106, 108 with angles 183, 233 of 3 degrees results in an overall angle 103 of 6 degrees.

Second member 108 can be readily separated from distal portion 104 by advancing actuating member 152 distally far enough to align engagement members with the enlarged distal end opening of actuator slots 244, 245. It is contemplated that instrument 100 can be provided in a kit with a number of second members 108 including outer surfaces 232 oriented at various angles 233 to allow the surgeon to attach a selected second member 108 with first member 106 to provide the desired overall angle 103. For example, FIG. 18A shows diagrammatically another second member 108 with outer surface 232 oriented at an angle 233 different than angle 233 of FIG. 18.

Instrument 100 can be used to distract and facilitate preparation of an intervertebral disc space for implantation of a spinal implant between the adjacent vertebrae. In a specific application, instrument 100 may be used to prepare an intervertebral disc space for insertion of the intervertebral disc prosthesis disclosed in U.S. patent application Ser. No. 10/042,589, filed on Jan. 9, 2002, and entitled Intervertebral Prosthetic Joint, the contents of which are hereby incorporated by reference in their entirety.

Figure 27:
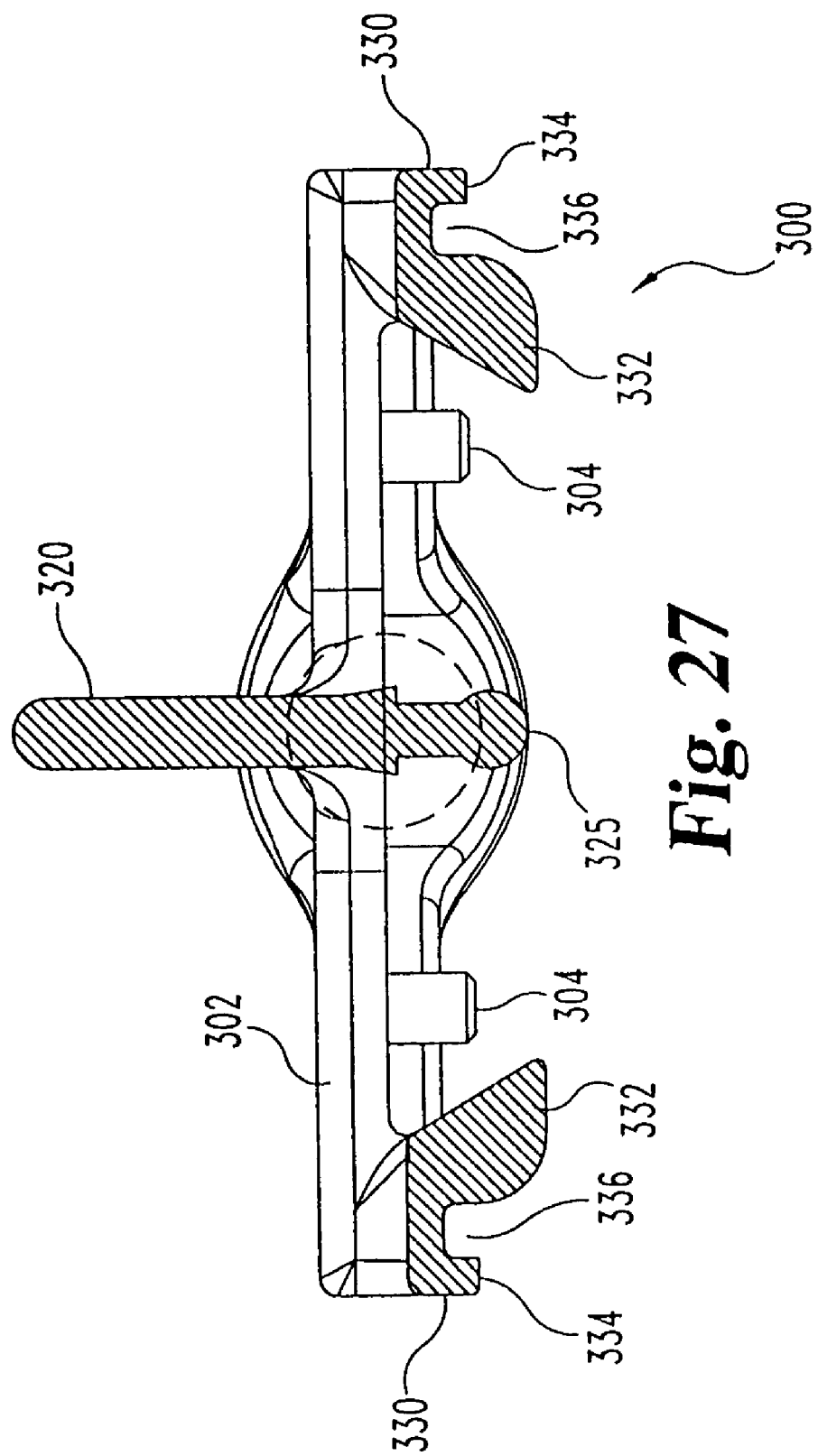
FIG. 27 is a section view through line 27-27 of FIG. 26.

Instrument 100 is adapted for use in conjunction with various surgical cutting instruments to prepare the adjacent vertebrae for insertion of a spinal implant therebetween. In such applications, instrument 100 also functions as a jig or guiding instrument for surgical instruments that serve to cut, shave, bore, or otherwise prepare the vertebral endplates and/or disc space for insertion and engagement of an implant. An example of one such instrument is a chisel 300, as depicted in FIGS. 25-27, and shown with instrument 100 in FIG. 24. Other examples include a keel chisel 400 as shown FIGS. 28-29, and a corner chisel 500 as shown in FIGS. 30-31.

To facilitate guided movement of the cutting instrument along distal portion 104, one or both of first and second members 106, 108 can each include one or more guiding features that interact with the cutting instrument to guide the cutting instrument along the outer surface of the first and second members 106, 108. For example, first member 106 includes beveled sidewalls 224, 226 extending along the outer lateral sides thereof as shown in FIGS. 10, 14. A first support member 225 extends along first sidewall 224, and a second support member extends along second sidewall 226. First member 106 further includes central keyway 192 as shown in FIG. 7. Similarly, second member 108 includes a first beveled sidewall 268 and an opposite second beveled sidewall 270 as shown in FIG. 20. A first support member 269 extends along first sidewall 268, and a second support member 271 extends along second sidewall 270. Second member 108 further includes central keyway 242 as shown in FIG. 15.

Actuating member 152 can be confined between first and second members 106, 108 by contact with inner lateral surfaces of the sidewalls. Alternatively or additionally, actuating member 152 can be confined between the sidewalls of first and second members 106, 108 by the engagement of the engagement members of actuating member 152 with the respective slots in first and second members 106, 108. Other embodiments contemplate actuating member 152 projecting laterally beyond one or both of the sidewalls of first and second members 106, 108.

Referring to FIGS. 25-27, combination chisel 300 includes a handle connector 310, a shaft assembly 315, a keel blade 320, and a pair of corner blades 330 extending along opposite sides of keel blade 320. Keel blade 320 is centrally located between corner blades 330, and cross member 302 extends between and interconnects corner blades 330 and keel blade 320 at their proximal ends. Pins 304 extend from cross member 302 and contact the proximal end of the first or second member 106, 108 to limit the insertion depth of chisel 300 relative thereto. Shaft assembly 315 includes first shaft portion 316 and second shaft portion 318 that extend from handle connector 310 to respective ones of the corner blades 330. Shaft assembly 315 forms a triangular opening with cross member 302 that facilitates visualization of the distal portion of the instrument assembly. Handle connector 310 provides a connection mechanism for removable connection of a handle that allows insertion and withdrawal of chisel 300. The handle can be removed to facilitate visualization during the surgical procedure.

Keel blade 320 includes distal cutting end 322 for penetrating the vertebral body and forming a vertically oriented slot in the vertebral body as keel blade 320 is advanced therein. Keel blade 320 includes a tapered proximal end 324 that extends to cross member 302. Chisel 300 also includes an elongated guiding fin 325 disposed generally opposite the keel blade 320, as shown in FIG. 27. Guiding fin 325 is configured to be slidably received within the corresponding keyway 192, 242 of the first or second member 106, 108, respectively. Guiding fin 325 extends downwardly from keel blade 320 and generally includes an enlarged end that fits within the keyway 192, 242 and restrains chisel 300 vertically relative thereto.

Figure 24:
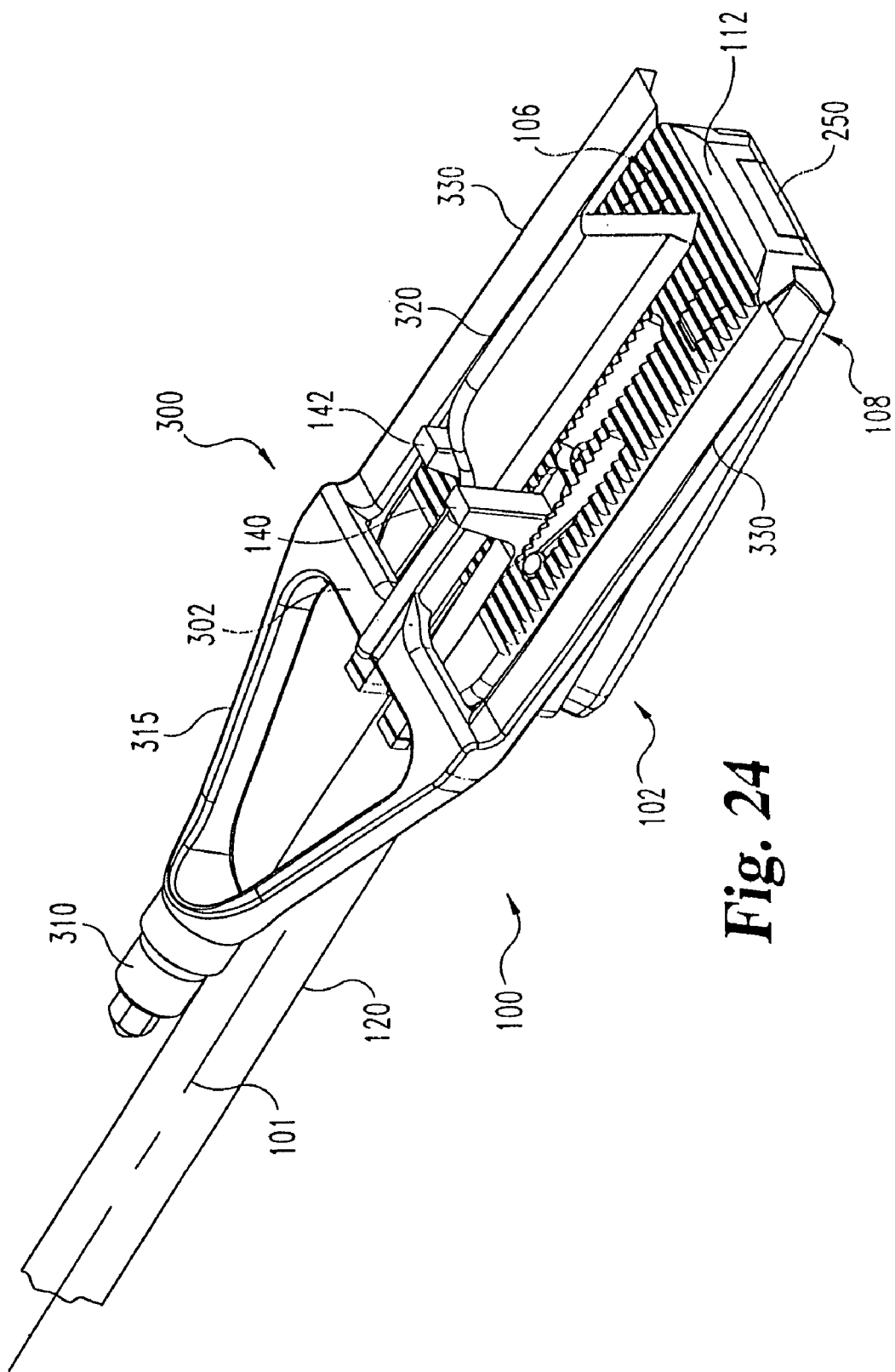
FIG. 24 is a perspective view of the distal portion of the instrument of FIG. 1 in an unexpanded configuration with a combination chisel positioned along a first member of the distal portion thereof.

Corner blades 330 each include a guide portion 332 that is received in the corresponding beveled sidewall 224, 226 of first member 106, and in the beveled sidewalls 268, 270 of second member 108, as shown in FIG. 24. Corner blades 330 further include a cutting portion 334 that includes a sharpened distal end 335 and forms channel 336 along guide portion 332. Channel 336 collects bone or other cut material removed by cutting portion 334 as chisel 330 is advanced along the respective first or second member 106, 108. The distal ends of keel blade 320 and corner blades 330 are shaped to make the cuts in the vertebral bodies so as to prepare the vertebral body to engage portions of the spinal implant positioned therein.

Figure 28:
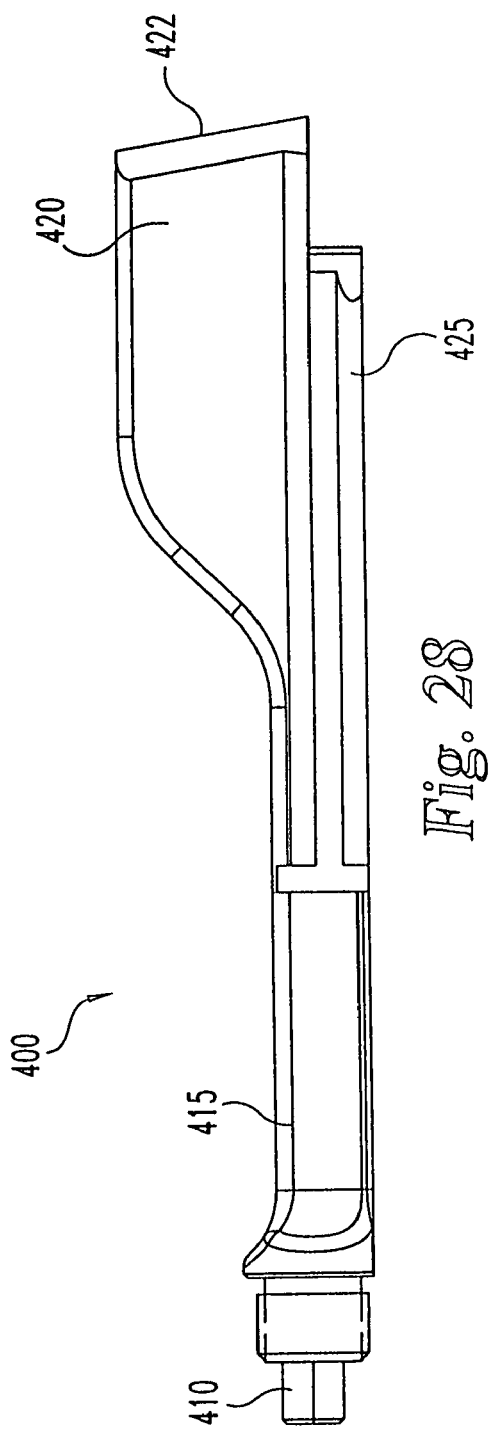
FIG. 28 is a side elevation view of a keel chisel.
Figure 29:
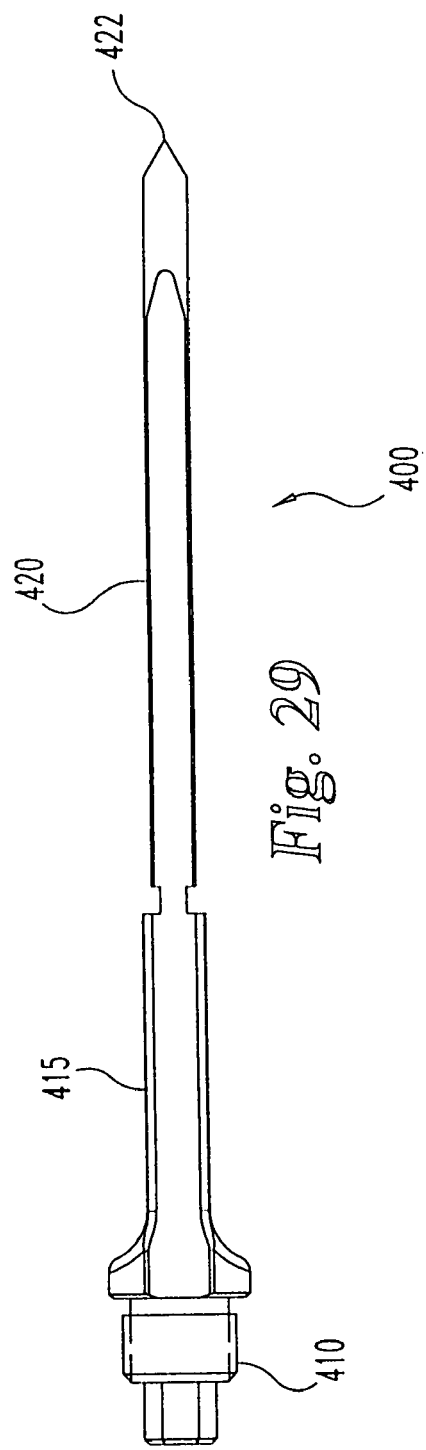
FIG. 29 is a plan view of the keel chisel of FIG. 28.
Figure 32:
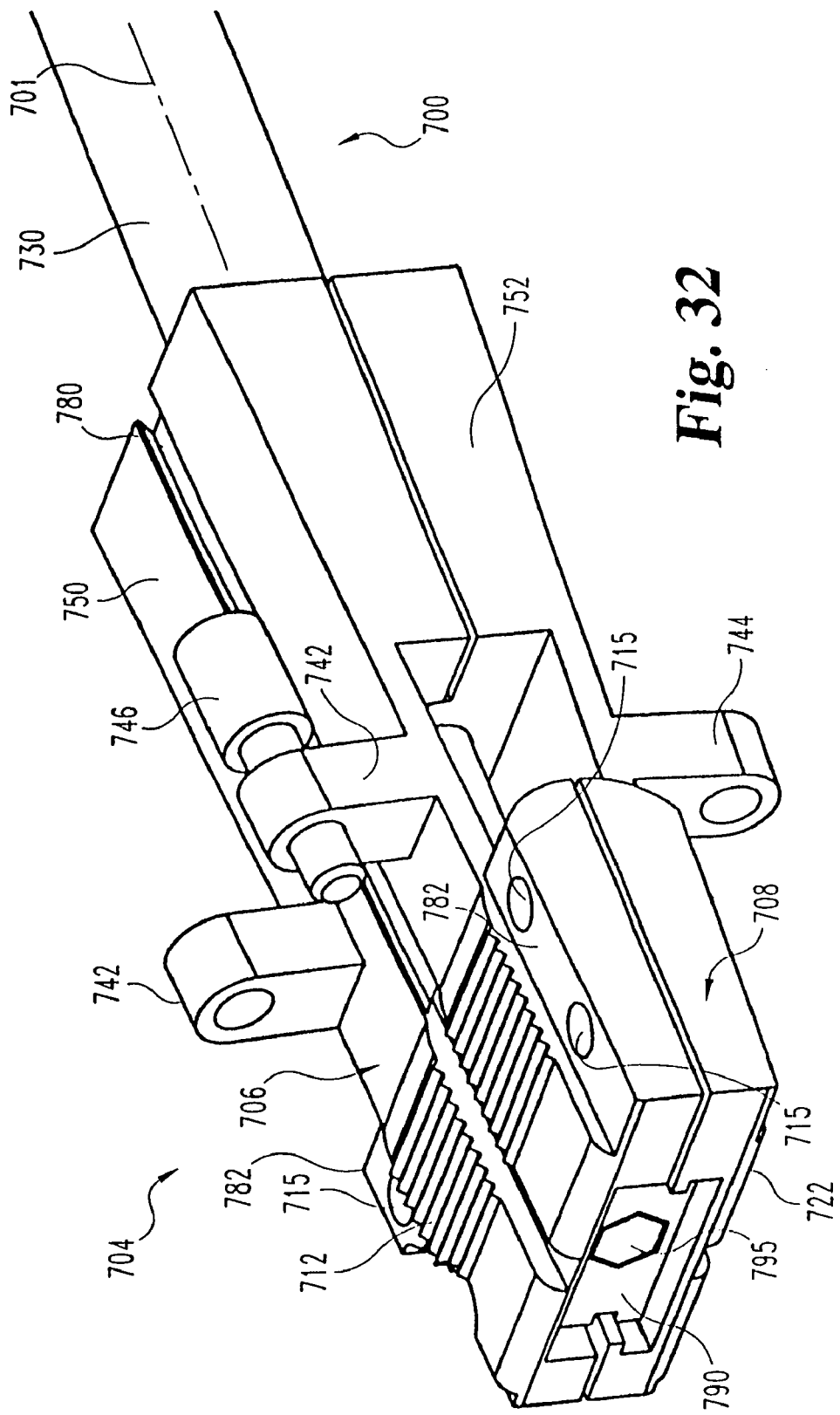
FIG. 32 is a perspective view of a distal portion of another embodiment instrument for distracting and facilitating preparation of an intervertebral space.
Figure 33:
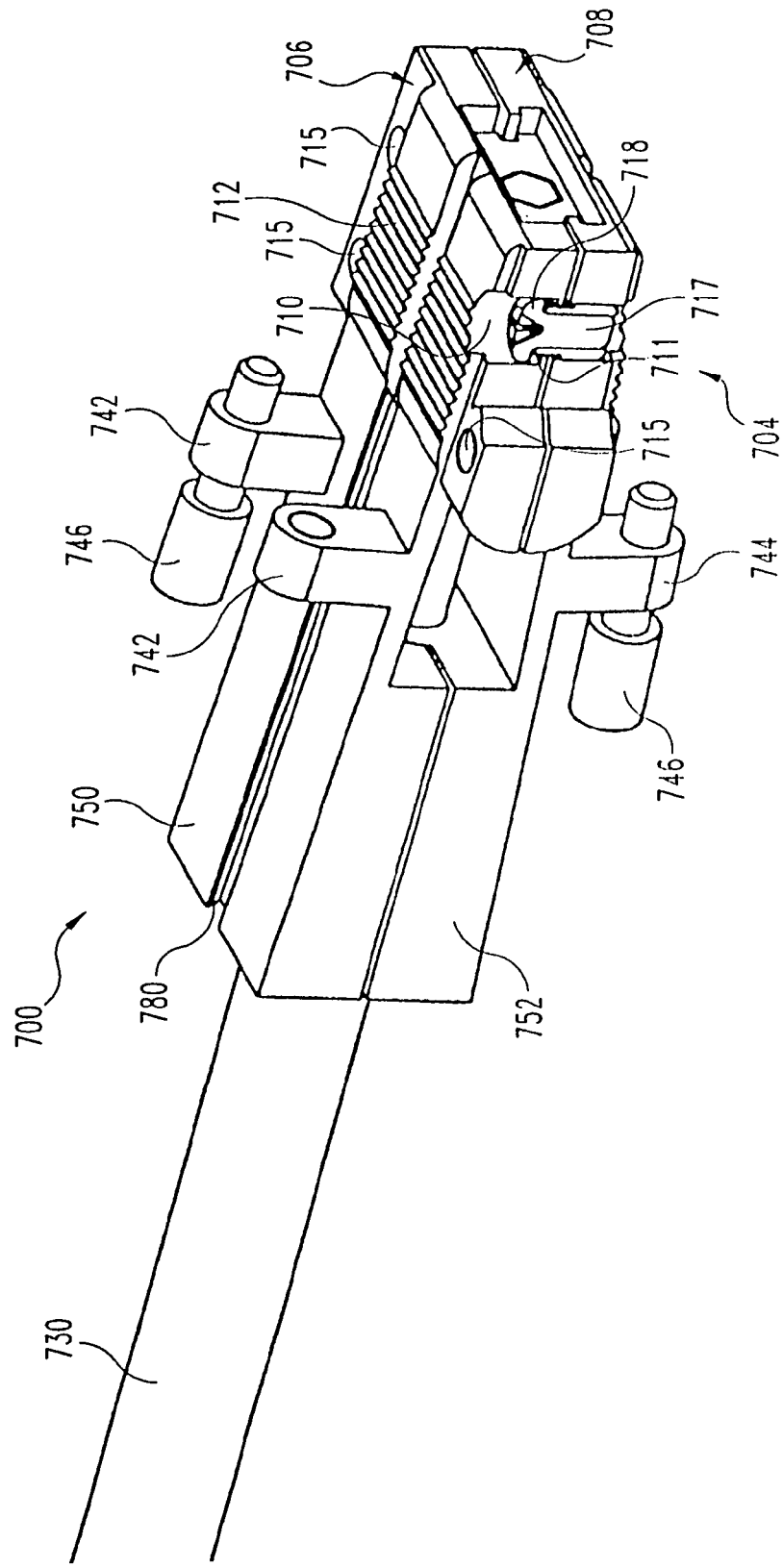
FIG. 33 is another perspective view of the distal portion of FIG. 32.
Figure 34:
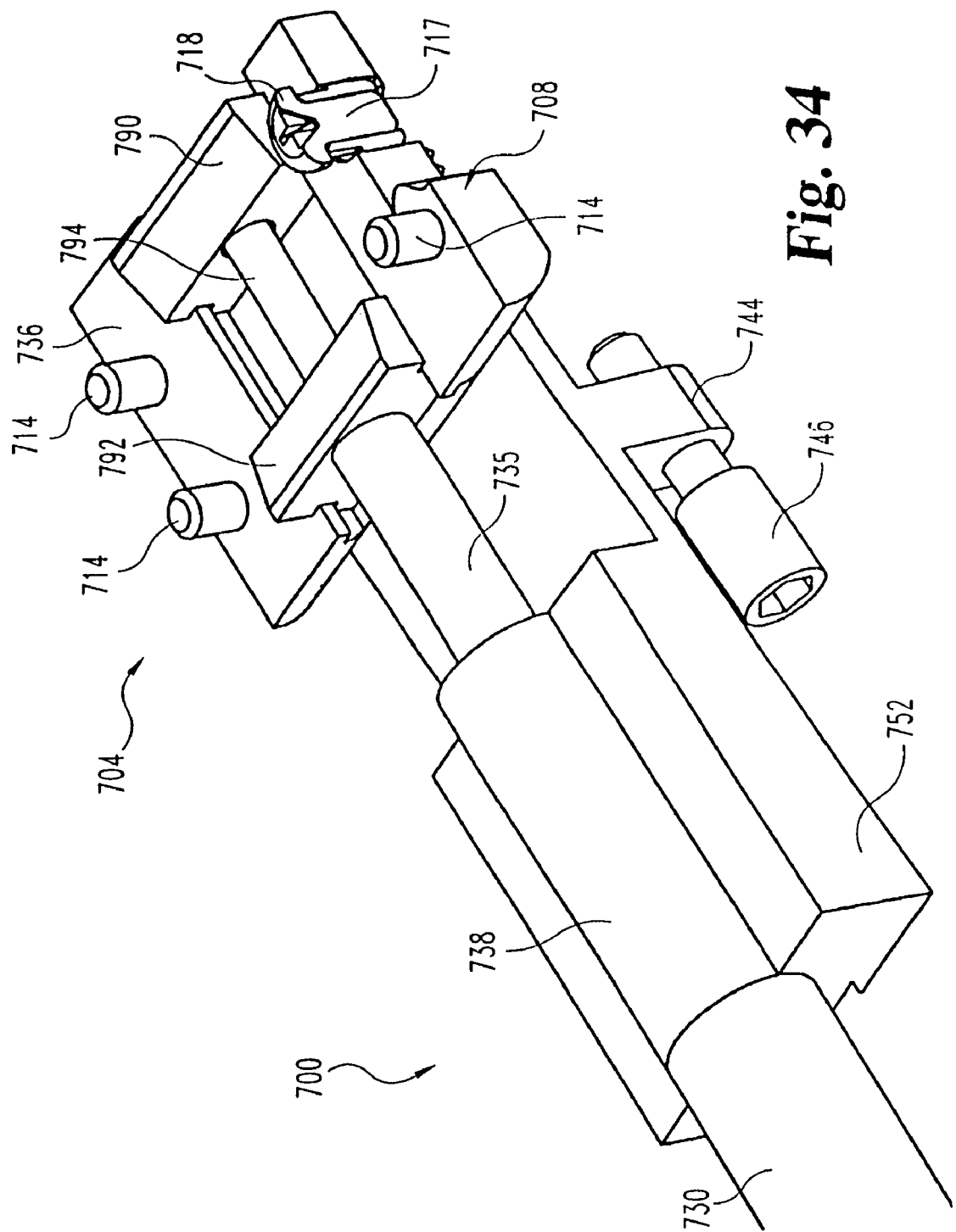
FIG. 34 is a perspective view of the distal portion in FIG. 32 with a second member of the distal portion removed.
Figure 35:
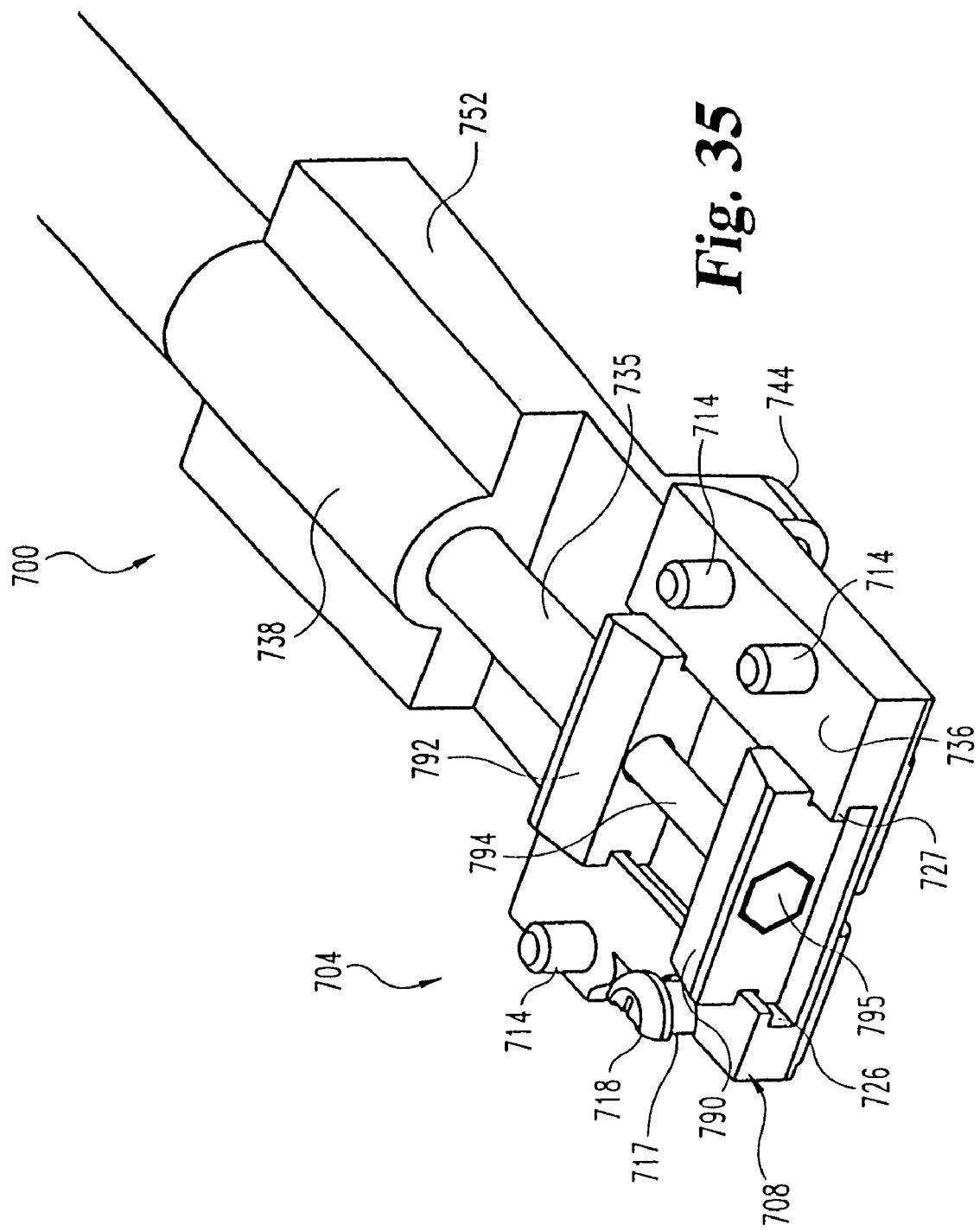
FIG. 35 is another perspective view of the distal portion in FIG. 32 with a second member of the distal portion removed.

It is further contemplated that separate keel chisels and corner chisels can be employed to provide the desired cut into the vertebral body along the first and second members 106, 108. For example, FIGS. 28 and 29 show a keel chisel 400 that includes a center keel blade 420. Keel blade 420 extends distally from a shaft 415, which includes a handle connector 410 at a proximal end thereof. A guiding fin 425 extends along the bottom of keel blade 420 and is adapted for positioning in keyways 192, 242 of first and second members 106, 108. Keel blade 420 includes a sharp blade 422 at a distal end thereof to form a vertically oriented slot in the vertebral body.

FIGS. 30 and 31 show a corner chisel 500 that includes a handle connector 510, a shaft assembly 515, a cross member 502 and corner blades 530. Corner blades 530 can be configured as discussed above with respect to corner blades 330 of combination chisel 300. Corner chisel 500 does not include any keel blade, and thus forms only corner cuts when guided along a respective one of first or second member 106, 108 positioned in the disc space.

In one example of a surgical procedure, instrument 100 and a pair of combination chisels 300 are used to prepare a disc space for insertion of a spinal prosthesis. From an anterior surgical approach, the distal portion 104 is inserted into a disc space with outer surfaces 182, 232 of first and second members 106, 108 oriented toward the adjacent vertebral endplate. A guide sleeve may be employed to provide a protected pathway to the disc space if desired.

The distal ends 112, 250 of first and second members 106, 108 of instrument 100 can be aligned, or nearly aligned, with the posterior edge of the vertebral bodies adjacent the anterior portion of the spinal canal. Such alignment may be used to ensure that the measurement provided by instrument 100 corresponds to the location where the disc prosthesis is to be placed. It should be understood that other prosthesis systems may require different alignments in the disc space. Proper positioning of instrument 100 may be confirmed with a lateral X-ray. If the X-ray and/or other observations indicate a different lordosis angle than the one provided by the selected instrument 100, instrument 100 is removed. Instrument 100 can then be modified by replacing second member 108 or by selecting a different instrument 100 that provides, for example, a different lordotic angle. The procedure is repeated until an acceptable lordosis angle is achieved.

Before positioning distal portion 104 in the disc space, or when the desired positioning in the disc space has been obtained and confirmed via a lateral X-ray, the stop members 140, 142 can be adjusted if necessary to engage against the outer surfaces of the vertebral bodies via rotation of the thumbwheel 138. Stop members 140, 142 prevent posterior movement of the instrument 100 during the remaining steps in the surgical procedure, protecting the spinal canal and nerve structures from impingement with instrument 100.

When distal portion 104 has been positioned in the desired location in the disc space, connector 128 is engaged with a T-handle or other tool and rotated to distally and axially advance inner shaft 124. This distally displaces actuating member 152 and separates first and second members 106, 108 to provide the desired distraction. Actuating member 152 is positioned along the portion of first and second members 106, 108 that are positioned in the disc space. Thus cantilevering of the portions of first and second members 106, 108 distally of actuating member 152 is minimized, providing uniform separation of the adjacent vertebrae along the length of first and second members 106, 108. The desired distraction can be predetermined, and measured during the procedure by distraction indicator 132. Alternatively or additionally, first and second members 106, 108 are expanded to tension the annulus fibers to firmly seat instrument 100 against the adjacent vertebral endplate in the intervertebral disc space.

The distraction height is measured, and if acceptable, disc preparation tools, such as one of chisel instruments discussed above, are positioned adjacent one of the first and second members 106, 108 and advanced distally therealong to prepare the disc space and adjacent vertebrae for insertion of an implant. The engagement of first and second members 106, 108 with the vertebral endplates and precise control over the distraction distance provided by instrument 100 allows the cuts made by the chisel to be uniform and precisely controlled. If additional surgical preparation of the disc space or vertebrae is desired, surgical tools not guided by first and second members 106, 108 may be employed with distal portion inserted in the space or removed therefrom.

The chisels discussed herein provide a variety of chiseling patterns that may be employed by the surgeon during the surgical procedure. One exemplary chiseling pattern includes driving keel blade 420 of keel chisel 400 into either the superior or the inferior vertebral body. The chisel handle can be removed, temporarily leaving keel blade 420 in the vertebral body to control bleeding and to improve surgical visibility. Either a keel chisel 400 or a combination keel/corner chisel 300 is then driven into the opposite vertebral body. If only a keel chisel 400 is employed initially in the opposite vertebral body, it can be followed by a corner chisel 500. The handles of the one or more chisels in the opposite vertebral body can then be removed to facilitate visualization and access to the first vertebral body. Finally, a corner chisel 500 can be driven into first vertebral body where keel chisel 400 is maintained. All chisels are then removed.

After the all the chisels have been removed, first and second members 106, 108 are moved toward their unexpanded configuration and distal portion 104 of instrument 100 is removed from the disc space. One or more shims or other temporary distractor(s) may be positioned between the adjacent vertebral bodies prior to removal of instrument 100 to maintain distraction while the spinal implant is inserted in the disc space. The implant can include upper and lower portions that fit within the spaces in the adjacent vertebral body provided by removal of the bone material with the chisels. The implant is then impacted into the prepared site and the shims or other temporary distractors are removed if employed.

Instrument 100 allows the lateral surgical exposure during the preparation of the disc space and vertebral bodies to be maintained at exactly or nearly exactly the width of the prosthesis being implanted. Actuating member 152 includes a width so that it is contained within first and second member 106, 108. The corner chisel cuts, which can correspond to the outer lateral perimeter of the prosthesis, are provided by the corner chisel blades. First and second members 106, 108 can be provided with a width that is substantially equal to or slightly less than the width of the spinal implant, thus a larger surgical exposure is not required for insertion first and second members 106, 108 than is required for insertion of the implant. However, while additional lateral exposure beyond that dictated by the implant size is not necessary, it may be employed if desired.

It is to be understood a wide variety of uses for instrument 100 are contemplated. Instrument 100 may be employed for disc space distraction and vertebral body preparation for insertion of one or more fusion cages, artificial discs, bone spacers, or other devices positionable in the spinal disc space. Instrument 100 can be adapted for use in any approach to the disc space, including anterior, lateral, anterior-oblique, postero-lateral, and transforaminal approaches.

Referring to FIGS. 32-39, another embodiment of an instrument 700 for distracting adjacent vertebrae is shown. Instrument 700 includes a distal portion 704 positionable in the disc space in an unexpanded configuration and movable to an expanded configuration to distract or separate the adjacent vertebrae. Instrument 700 can be employed as a jig or guiding instrument in the manner discussed above with respect to instrument 100, and can include any of the features of instrument 100. Instrument 700 extends along a longitudinal axis 701 and includes a handle assembly 702 extending proximally from distal portion 704.

Figure 37:
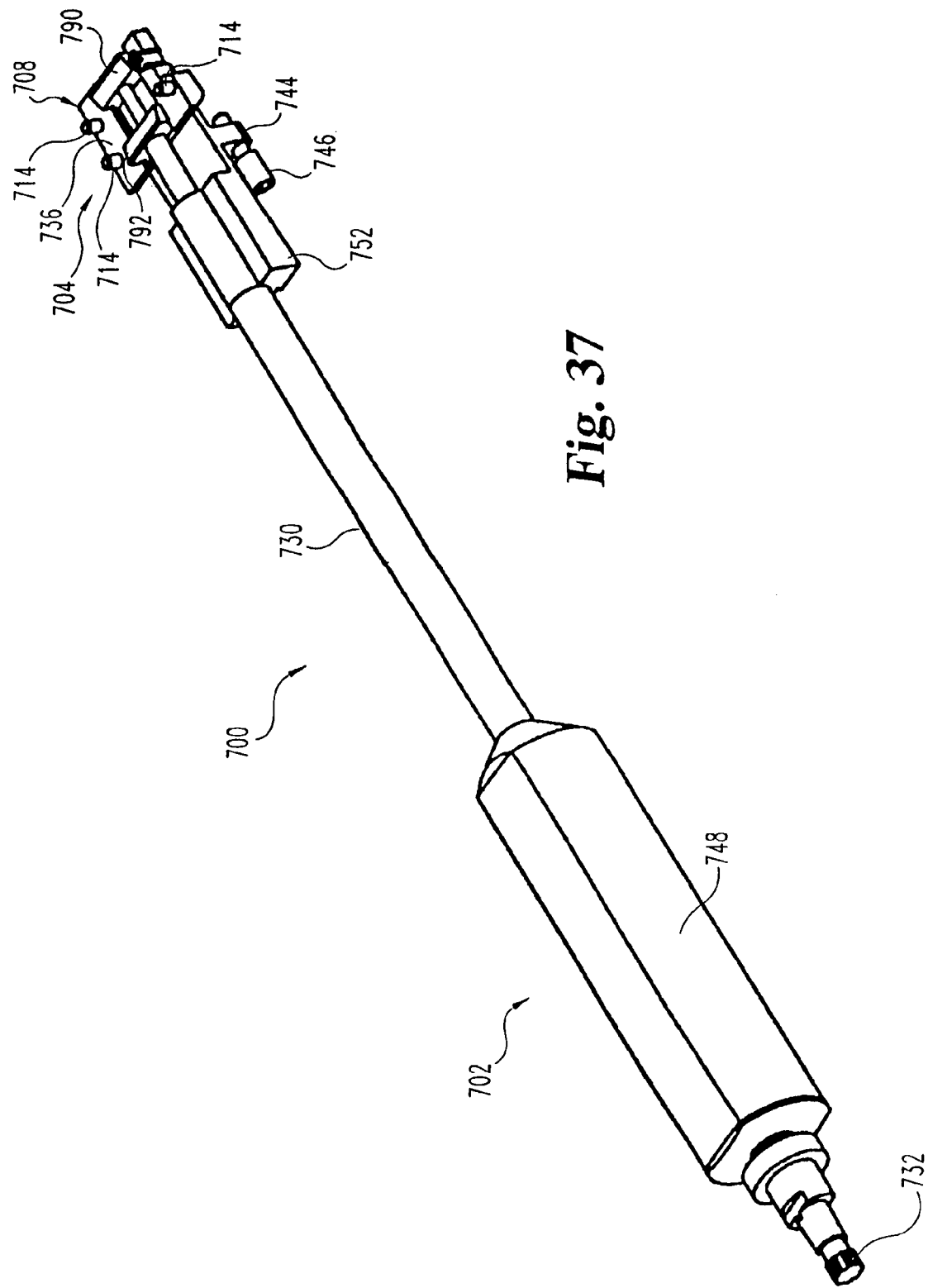
FIG. 37 is a perspective view of the instrument including the distal portion in FIG. 32 with a second member of the distal portion removed.
Figure 38:
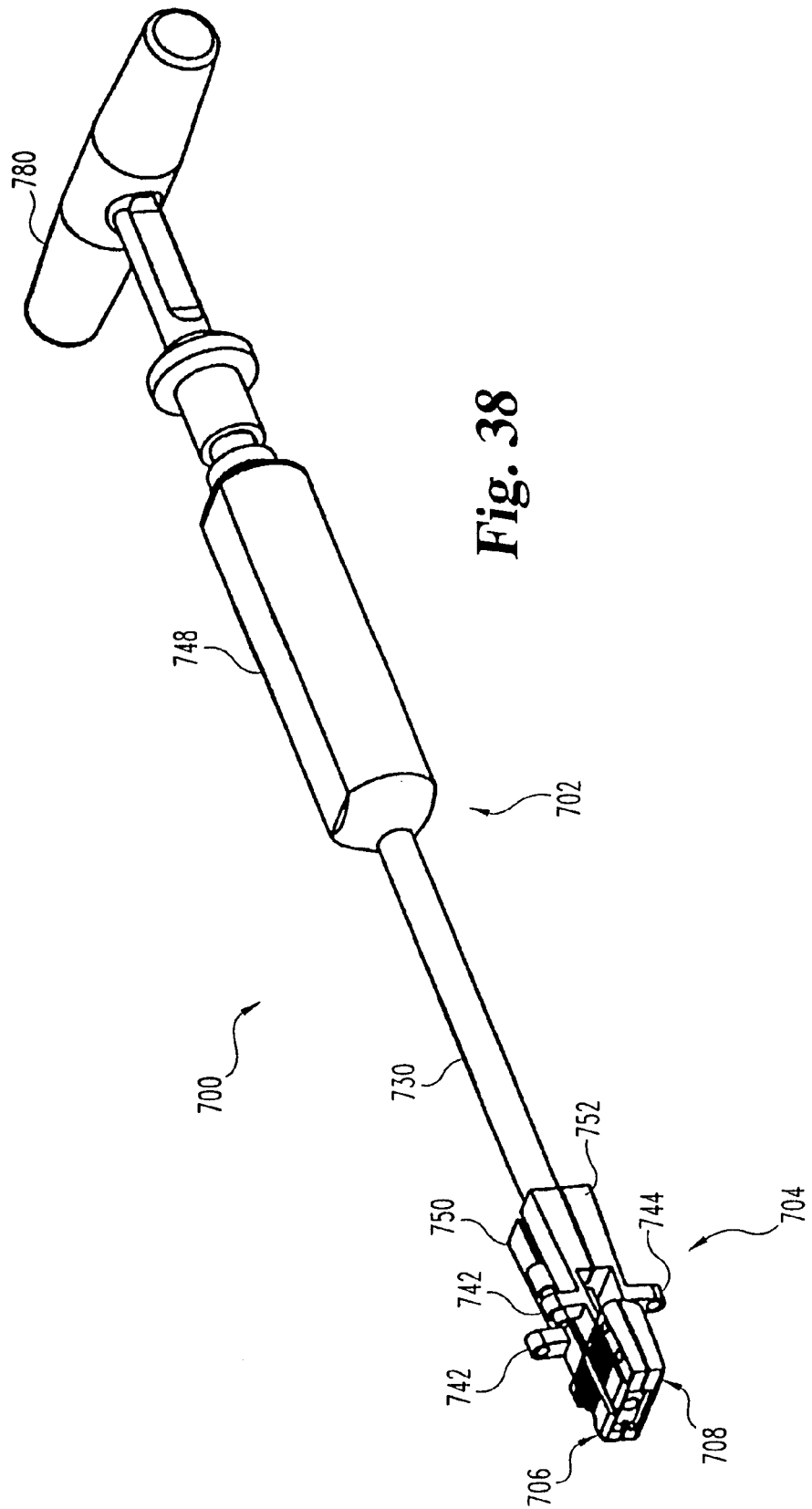
FIG. 38 is a perspective view of the instrument including the distal portion in FIG. 32 and a T-handle coupled to the proximal end thereof.
Figure 39:
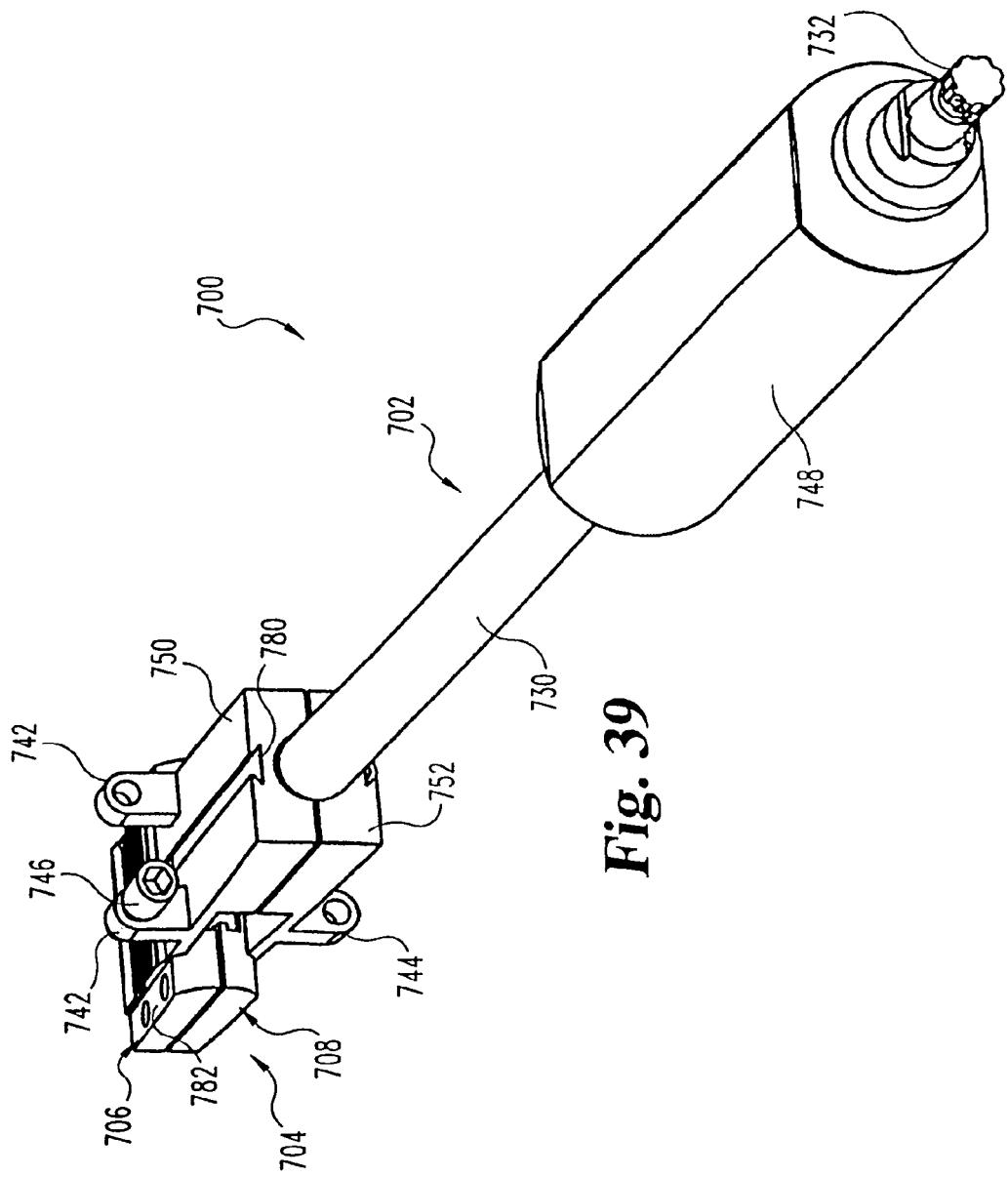
FIG. 39 is another perspective view of the instrument of FIG. 38 with the T-handle removed.

Distal portion 704 includes a first member 706 and a second member 708. As shown in FIGS. 37-29, handle assembly 702 includes a proximal gripping portion 748 and an elongate outer shaft 730 that is coupled to and extends distally from gripping portion 748. An inner shaft 735 is rotatably positioned in outer shaft 730, and includes a proximal end coupling member 732 adapted to engage, for example, a T-handle 780.

When assembled, first and second members 706, 708 define a pair of opposed outer engaging surfaces 712, 722. Engaging surfaces 712, 722 contact the adjacent vertebral endplates and exert a distraction force thereon when first and second members 706, 708 are separated from one another. Engaging surfaces 712, 722 can include recesses or other surface features to facilitate engagement with the adjacent vertebral endplate. Engaging surfaces 712, 722 can also be angled relative to one another, or parallel to one another, as discussed above with respect to instrument 100.

First member 706 is coupled to second member 708 with alignment posts 714 extending from an inner surface 736 of second member 708. Three alignment posts are shown, although less than three or more than three alignment posts are also contemplated. Alignment posts 714 are received within the corresponding alignment openings 715 extending through first member 706, and resist first and second members 706, 708 from twisting relative to one another. A fastener 717 is secured to second member 708 and includes an enlarged head captured in receptacle 710 of first member 706. Receptacle 710 includes a inner flange 711 that contacts the enlarged head of fastener 717 to limit the movement of first member 706 away from second member 708 and to retain first and second members 706, 708 together. Fastener 717 can be adjusted to position the enlarged head 718 relative to second member 708 to provide the desired maximum distraction height.

The outer shaft 730 includes a passage therethrough through which an inner shaft 735 extends. Inner shaft 735 is operable with T-handle 780 to actuate a distal actuating member 790 and a proximal actuating member 792 positioned about an actuator shaft 794. Proximal actuating member 792 is slidable on actuator shaft 794. Actuator shaft 794 includes a hexagonal head 795 at a distal end thereof non-rotatably received in distal actuating member 790. As inner shaft 735 is threaded or otherwise advanced distally along actuator shaft 794, the distal end of inner shaft 735 bears against and pushes proximal actuating member 792 distally and actuator shaft 794 simultaneously pulls distal actuating member 790 proximally.

Figure 36:
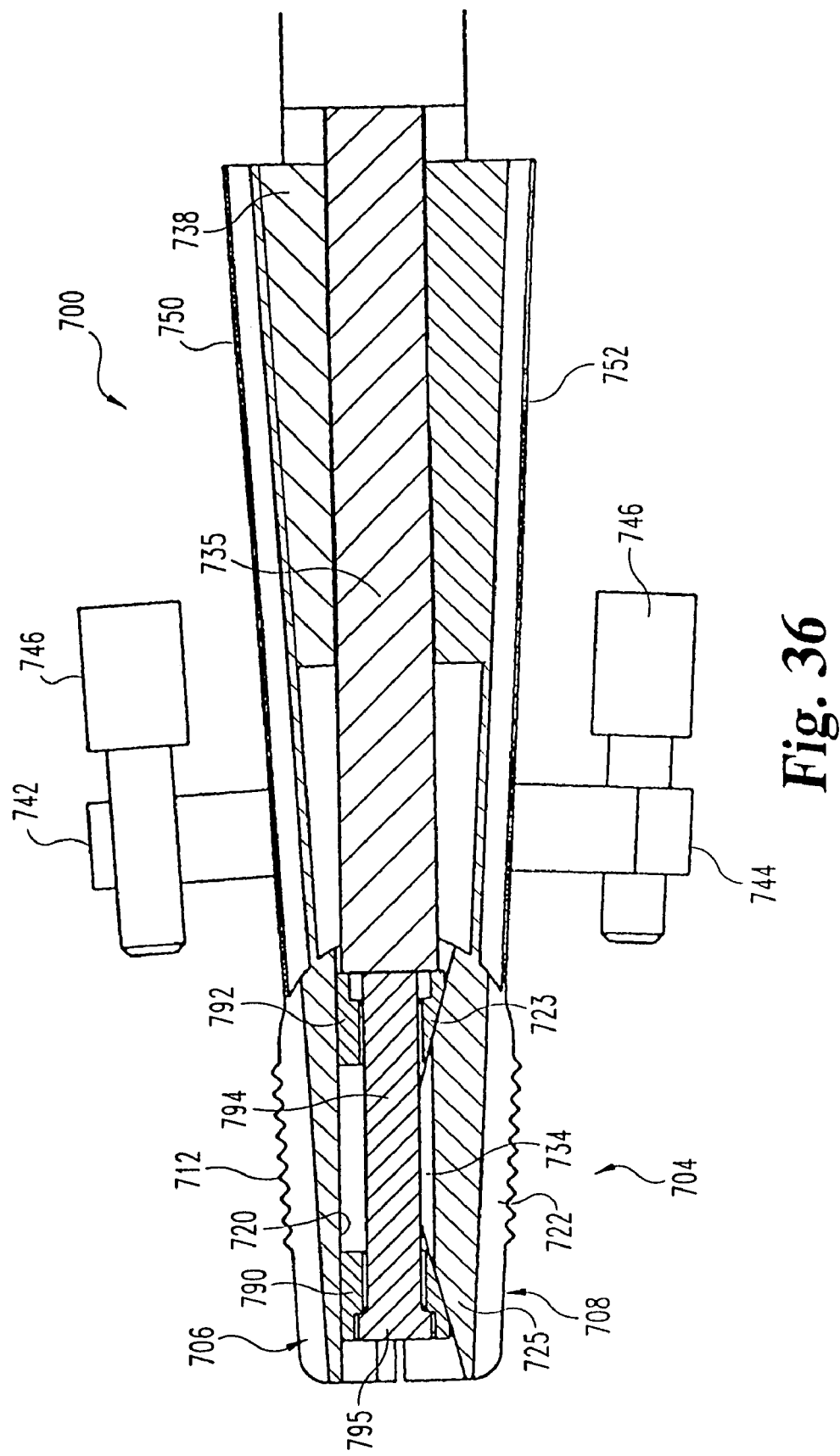
FIG. 36 is a section view through the distal portion of FIG. 32.

This movement initiated through rotation of inner shaft 735 forces actuating members 790, 792 together along actuator shaft 794 and along inner surface 720 of first member 706, and also along distal inner cam surface 725 and proximal inner cam surface 723 of second member 706 as shown in FIG. 36. The inner cam surfaces 723, 725 are inclined toward one another and meet at an apex therebetween. The inclined cam surfaces 723, 725 displace actuating members 790, 792 moving therealong toward first member 706 and cause first member 706 to move away from second member 708. A notch 734 in cam surfaces 723, 725 accommodates actuator shaft 794. The sides of each actuating member 790, 792 are slottedly engaged with rails 726, 727 of second member 708 to maintain actuating members 790, 792 in engagement with second member 708 and to restrict lateral movement of actuating members 790, 792.

First member 706 includes a pair of outwardly extending arms 742. Arms 742 each define a hole that receives a positive stop 746. Stop 746 is threadedly received inside the hole such that stop 746 is adjustable relative to first member 706, and extend distally from arms 742 to abut the vertebral body when positioned thereagainst. Stops 746 can be adjusted to adjust the insertion depth of distal portion 704 in the disc space. Second member 708 can similarly include a pair of outwardly extending arms 744 for receiving a threaded positive stop.

Each of first and second members 706, 708 can include means for guiding engagement with disc preparation and/or vertebral body instruments. First member 706 includes a proximal mounting portion 750 that extends along a distal portion of outer shaft 730. Second member 708 includes a proximal mounting portion 752 that extends along a distal portion of outer shaft 730 and includes a mounting member 738 mounted with outer shaft 730. Proximal mounting portion 750 is movable relative to outer shaft 730 and proximal mounting portion 752 in response to the expansion of first member 706 with actuating members 790, 792.

Proximal mounting portion 750 includes a central keyway 780. Keyway 780 can include a dovetail configuration with a pair of angled surfaces converging towards a narrower opening along the outer surface of proximal mounting portion 750. Keyway 780 can receive a guiding fin of a keel chisel, such as is provided with keel chisel 400 or combination chisel 300 discussed above. Support for the corner blades of a corner chisel, or of the corner blades of a combination chisel, can be provided by lateral surfaces 782 of first member 706. Lateral surfaces 782 are offset below engaging surface 712 to facilitate passage of the corner blade therealong. Proximal mounting portion 752 can similarly be provided with a central keyway and lateral surfaces offset from engaging surfaces 722. Arms 742, 744 can contact the chisel to limit the insertion depth of the chisel blades into the disc space.

While the invention has been illustrated and described in detail in the drawings and foregoing description, the same is to be considered illustrative and not restrictive in character. All changes, equivalents, and modifications that come within the scope of the invention described herein are desired to be protected.

What is claimed is:

1. An instrument for separating adjacent vertebrae, comprising:
    a first member positonable along an endplate of one of the adjacent vertebrae and including a first outer surface extending between a proximal end and a distal end;
    a second member positonable along an endplate of the other of the adjacent vertebrae, said second member being movable relative to said first member and including a second outer surface extending between a proximal end and a distal end, wherein said first and second outer surfaces are tapered relative to one another from said proximal ends to said distal ends to form an angle between said first and second outer surfaces;
    a handle assembly extending proximally from said first and second members; and
    at least one actuating member positioned between said first and second members, said at least one actuating member including a wedge shaped body with opposite first and second surfaces tapering toward one another at a taper angle and contacting respective ones of said first and second members, wherein said taper angle of said first and second surfaces is substantially greater than said angle between said first and second outer surfaces, said at least one actuating member being movable with said handle assembly from a first position wherein said first and second members include an unexpanded configuration relative to one another for insertion in the space between adjacent vertebrae to a second position providing an expanded configuration wherein said actuating member displaces at least one of said first and second members away from the other of said first and second members and said angle between said first and second outer surfaces is maintained, wherein:
    said first and second members each include a cam surface in contact with respective ones of said first and second surfaces of said actuating member;
    said body of said actuating member includes a pair of engagement members extending from said second surface;
    said second member includes a pair of actuator slots extending along a central axis of said second member, said pair of engagement members being slidably received in a corresponding one of said actuator slots of said second member; and
    said actuator slots each include an intermediate surface in contact with an enlarged head of said engagement member positioned therein.

2. The instrument of claim 1, wherein said first and second outer surfaces are positionable against an endplate of an adjacent vertebra.

3. The instrument of claim 2, wherein said first and second outer surfaces each include a plurality of engagement recesses therein.

4. The instrument of claim 2, wherein said angle between said first and second outer surfaces corresponds to a lordotic angle between the adjacent vertebrae.

5. The instrument of claim 4, wherein said first and second outer surfaces taper toward one another distally and said angle is selected from the group consisting of: 6 degrees, 9 degrees, and 12 degrees.

6. The instrument of claim 1, wherein said cam surfaces are each inclined along an angle that corresponds to an angle of the adjacent first or second surface relative to a longitudinal axis of the instrument.

7. The instrument of claim 1, wherein said intermediate surface extends into said second member parallel to said second surface of said body of said actuating member.

8. The instrument of claim 7, wherein said intermediate surface is positioned adjacent an outer surface of said second member at a proximal end of said actuator slot and positioned adjacent an inner surface of said second member at a distal end of said actuator slot.

9. The instrument of claim 8, wherein said actuator slots each include an enlarged opening at said distal end thereof sized to allow passage of said enlarged head of said engagement member positioned therein to pass therethrough to uncouple said second member from said actuating member.

10. The instrument of claim 1, wherein:
    one of said first and second members includes at least one post adjacent a proximal end thereof extending toward the other of said first and second members; and
    the other of said first and second members includes at least one receiving member adjacent a proximal end thereof, said receiving member including a passage aligned with and movably receiving said post.

11. The instrument of claim 10, wherein:
said at least one post includes a pair of posts positioned on opposing sides of a central axis of said one of said first and second members; and
said at least one receiving member includes a pair of receiving members positioned on opposing sides of a central axis of said other of said first and second members.

12. The instrument of claim 1, wherein said first and second members each include opposing sidewalls extending therealong and said actuating member is confined between said opposing sidewalls.

13. An instrument for separating adjacent vertebrae, comprising:
a first member positionable along an endplate of one of the adjacent vertebrae;
a second member positionable along an endplate of the other of the adjacent vertebrae, said second member being movable relative to said first member;
a handle assembly extending proximally from said first and second members; and at least one actuating member positioned between said first and second members, said at least one actuating member being movable with said handle assembly from a first position wherein said first and second members include an unexpanded configuration relative to one another for insertion in the space between adjacent vertebrae to a second position providing an expanded configuration wherein said actuating member displaces at least one of said first and second members away from the other of said first and second members, wherein:
said first member includes a pair of grooves opening toward a proximal end of said first member, said grooves being adapted to receive respective ones of a first arm of a first stop member and a second arm of a second stop member, said first and second arms being adjustable in said grooves to position said first and second stop members at a desired location relative to said first member; and
said handle assembly includes an intermediate shaft and an outer shaft movable along said intermediate shaft, said first and second arms extending from a distal end of said outer shaft, wherein said handle assembly further comprises an inner shaft extending through said intermediate shaft, said inner shaft including a distal end coupled to said at least one actuating member and a proximal end coupled with a connector, wherein said connector is operable to selectively move said inner shaft axially relative to said intermediate shaft.

14. The instrument of claim 13, wherein said handle assembly includes a handle fixed to a proximal end of said intermediate shaft and said outer shaft is coupled with an adjustment mechanism at said handle, said adjustment mechanism operable to move said outer shaft axially along said intermediate shaft.

15. The instrument of claim 14, wherein said adjustment mechanism includes a thumbwheel threadingly coupled about a proximal end of said outer shaft.

16. The instrument of claim 13, wherein said first member is fixed to said intermediate shaft of said handle assembly and said second member is removably coupled to said first member with said actuating member.

17. An instrument for separating adjacent vertebrae, comprising:
a first member including a first bone contacting surface positionable along an endplate of one of the adjacent vertebrae;
a second member including a second bone contacting surface positionable along an endplate of the other of the adjacent vertebrae, said second member being movable relative to said first member;
a handle assembly extending proximally from said first and second members; and
at least one actuating member positioned between said first and second members, said at least one actuating member being movable with said handle assembly from a first position wherein said first and second members include an unexpanded configuration relative to one another for insertion in the space between adjacent vertebrae to a second position providing an expanded configuration wherein said actuating member displaces at least one of said first and second members away from the other of said first and second members;
wherein said first member extends along a central axis and includes:
a pair of lateral actuator slots positioned on opposite sides of said central axis; and a pair of medial actuator slots positioned on opposite sides of said central axis and offset from said lateral slots toward said central axis, wherein said medical and lateral actuator slots open along said first bone contacting surface of said first member and said actuating member includes a first pair of engagement members slidably received in respective ones of said lateral slots and a second pair of engagement members slidably received in respective ones of said medial slots, wherein said first and second pair of engagement members move along said medial and lateral actuator slots and away from said bone contacting surface of said first member as said first and second members move from said unexpanded configuration to said expanded configuration.

18. The instrument of claim 17, wherein each of said actuator slots includes an intermediate surface and each of said engagement members includes an enlarged head slidably received along a respective one of said intermediate surfaces to secure said actuating member thereto.

19. The instrument of claim 18, wherein each of said actuator slots is inclined in said first member from a position adjacent an outer surface of said first member at a proximal end of said actuator slot to a position adjacent an inner surface of said first member at a distal end of said actuator slot.

20. The instrument of claim 19, wherein said lateral actuator slots are offset proximally from said medial actuator slots and said first pair of engagement members are offset proximally of said second pair of engagement members.

21. An instrument for separating adjacent vertebrae, comprising:
a first member positionable along an endplate of one of the adjacent vertebrae and including a first outer surface extending between a proximal end and a distal end;
a second member positionable along an endplate of the other of the adjacent vertebrae, said second member being movable relative to said first member and including a second outer surface extending between a proximal end and a distal end, wherein said first and second outer surfaces are tapered relative to one another from said proximal ends to said distal ends to form an angle between said first and second outer surfaces;
a handle assembly extending proximally from said first and second members; and
at least one actuating member positioned between said first and second members, said at least one actuating member including a wedge shaped body with opposite first and second surfaces tapering toward one another at a taper angle and contacting respective ones of said first and second members, wherein said taper angle of said first and second surfaces is substantially greater than said angle between said first and second outer surfaces, said at least one actuating member being movable with said handle assembly from a first position wherein said first and second members include an unexpanded configuration relative to one another for insertion in the space between adjacent vertebrae to a second position providing an expanded configuration wherein said actuating member displaces at least one of said first and second members away from the other of said first and second members and said angle between said first and second outer surfaces is maintained, wherein said handle assembly includes an inner shaft extending proximally from and coupled to said actuating member and an intermediate shaft about said inner shaft, said intermediate shaft coupled with said first member, said inner shaft longitudinally movable in said intermediate shaft to move said actuating member relative to said first and second members.

22. The instrument of claim 21, further comprising an outer shaft about said intermediate shaft, said outer shaft including at least one stop member extending therefrom adjacent said first member, said outer shaft adjustably positionable along said intermediate shaft to adjust a position of said at least one stop member relative to said first member.

23. An instrument for separating adjacent vertebrae, comprising:
a first member positionable along an endplate of one of the adjacent vertebrae;
a second member positionable along an endplate of the other of the adjacent vertebrae, said second member being movable relative to said first member;
a handle assembly extending proximally from said first and second members; and at least one actuating member positioned between said first and second members, said at least one actuating member being movable with said handle assembly from a first position wherein said first and second members include an unexpanded configuration relative to one another for insertion in the space between adjacent vertebrae to a second position providing an expanded configuration wherein said actuating member displaces at least one of said first and second members away from the other of said first and second members, wherein said handle assembly includes an inner shaft extending proximally from and coupled to said actuating member and an intermediate shaft about said inner shaft, said intermediate shaft coupled with said first member, said inner shaft longitudinally movable in said intermediate shaft to move said actuating member relative to said first and second members, and further comprising a distraction indicator coupled to said inner shaft, said distraction indicator moving longitudinally with said inner shaft in said intermediate shaft in accordance with a position of said actuating member relative to said first and second members, said distraction indicator being viewable along a proximal portion of said handle assembly and providing an indication of a distraction height, said distraction height corresponding to a separation of said first and second members imparted by said actuating member.

24. An instrument for separating adjacent vertebrae, comprising:
a first member positionable along an endplate of one of the adjacent vertebrae and including a first outer surface extending between a proximal end and a distal end;
a second member positionable along an endplate of the other of the adjacent vertebrae, said second member being movable relative to said first member and including a second outer surface extending between a proximal end and a distal end, wherein said first and second outer surfaces are tapered relative to one another from said proximal ends to said distal ends to form an angle between said first and second outer surfaces;
a handle assembly extending proximally from said first and second members; and at least one actuating member positioned between said first and second members, said at least one actuating member including a wedge shaped body with opposite first and second surfaces tapering toward one another at a taper angle and contacting respective ones of said first and second members, wherein said taper angle of said first and second surfaces is substantially greater than said angle between said first and second outer surfaces, said at least one actuating member being movable with said handle assembly from a first position wherein said first and second members include an unexpanded configuration relative to one another for insertion in the space between adjacent vertebrae to a second position providing an expanded configuration wherein said actuating member displaces at least one of said first and second members away from the other of said first and second members and said angle between said first and second outer surfaces is maintained, wherein said second member comprises a plurality of second members, each of said plurality of second members being removably engageable to said first member.

25. The instrument of claim 24, wherein said angle between said first and second outer surfaces is different for each of said plurality of second members.

26. An instrument for separating adjacent vertebrae, comprising:
a first member positionable along an endplate of one of the adjacent vertebrae;
a second member positionable along an endplate of the other of the adjacent vertebrae, said second member being movable relative to said first member, said first and second members including outer bone contacting surfaces facing in opposite directions;
a handle assembly extending proximally from said first and second members; and
at least one actuating member positioned between said first and second members, said at least one actuating member being movable with said handle assembly from a first position wherein said first and second members include an unexpanded configuration relative to one another for insertion in the space between adjacent vertebrae to a second position providing an expanded configuration wherein said actuating member displaces at least one of said first and second members away from the other of said first and second members to position said outer bone contacting surfaces in contact with the adjacent vertebrae, wherein at least one of said first and second members includes a central keyway opening along said outer bone contacting surface thereof adapted to receive a guiding fin of a cutting instrument movable therealong, wherein:
said at least one of said first and second members includes opposite sidewalls adapted to receiving guide portions of corner blades of the cutting instrument movable therealong; and
said opposite sidewalls are beveled from an outer surface of said at least one of said first and second members toward a central axis of said at least one of said first and second members, and said at least one of said first and second members comprising a support member adjacent an inner surface thereof extending alone at Least a portion of each of said sidewalls.

27. An instrument for separating adjacent vertebrae, comprising:
a first member positionable along an endplate of one of the adjacent vertebrae and including a first outer surface extending between a proximal end and a distal end;
a second member positionable along an endplate of the other of the adjacent vertebrae, said second member being movable relative to said first member and including a second outer surface extending between a proximal end and a distal end, wherein said first and second outer surfaces are tapered relative to one another from said proximal ends to said distal ends to form an angle between said first and second outer surfaces;
a handle assembly extending proximally from said first and second members; and
at least one actuating member positioned between said first and second members, said at least one actuating member including a wedge shaped body with opposite first and second surfaces tapering toward one another at a taper angle and contacting respective ones of said first and second members, wherein said taper angle of said first and second surfaces is substantially greater than said angle between said first and second outer surfaces, said at least one actuating member being movable with said handle assembly from a first position wherein said first and second members include an unexpanded configuration relative to one another for insertion in the space between adjacent vertebrae to a second position providing an expanded configuration wherein said actuating member displaces at least one of said first and second members away from the other of said first and second members and said angle between said first and second outer surfaces is maintained, wherein said at least one actuating member and said first and second members are configured so that the proximal ends of said first and second members and said distal ends of said first and second members move the same distance relative to one another as said actuating member is moved therebetween.

28. An instrument for separating adjacent vertebrae, comprising:
a first member positionable along an endplate of one of the adjacent vertebrae;
a second member positionable along an endplate of the other of the adjacent vertebrae, said second member movable relative to said first member; and
a handle assembly extending proximally from said first and second members along a longitudinal axis, said handle assembly including an intermediate shaft extending along said longitudinal axis with said intermediate shaft having a distal portion coupled to said first and second members, an outer shaft along said intermediate shaft and an adjustment mechanism coupled to said outer shaft, said outer shaft further including at least one stop member extending from a distal end thereof transversely to said longitudinal axis, said stop member being positionable in contact with one of the adjacent vertebrae to limit an insertion depth of said first and second members in the space between the adjacent vertebrae, said stop member being adjustable in the direction of said longitudinal axis relative to said first and second members by rotating said adjustment mechanism about said longitudinal axis to longitudinally adjust a position of said outer shaft relative to said intermediate shaft and thereby move said stop member in the direction of the longitudinal axis, wherein said at least one stop member extends from a distal end of said outer shaft.

29. The instrument of claim 28, further comprising at least one actuating member positioned between said first and second members, said at least one actuating member being movable from a first position wherein said first and second members include an unexpanded configuration relative to one another for insertion in the space between adjacent vertebrae to a second position wherein said actuating member displaces at least one of said first and second members away from the other of said first and second members to provide an expanded configuration.

30. The instrument of claim 28, wherein said handle assembly includes a handle member fixed to a proximal end of said intermediate shaft.

31. An instrument for separating adjacent vertebrae, comprising:
a first member positionable along an endplate of one of the adjacent vertebrae;
a second member positionable along an endplate of the other of the adjacent vertebrae, said second member movable relative to said first member;
a handle assembly extending proximally from said first and second members along a longitudinal axis, said handle assembly including at least one stop member extending from a distal end thereof transversely to said longitudinal axis, said stop member being positionable in contact with one of the adjacent vertebrae to limit an insertion depth of said first and second members in the space between The adjacent vertebrae, said stop member being adjustable in the direction of said longitudinal axis relative to said first and second members, wherein said handle assembly includes:
an intermediate shaft and an outer shaft movable along said intermediate shaft, said at least one stop member extending from a distal end of said outer shaft; and
a handle member fixed to a proximal end of said intermediate shaft and said outer shaft is coupled with an adjustment mechanism at said handle, said adjustment mechanism operable to move said outer shaft along said intermediate shaft, wherein said adjustment mechanism includes a thumbwheel threadingly coupled about a proximal end of said outer shaft, wherein said thumbwheel is housed in said handle.

32. The instrument of claim 31, wherein said outer shaft includes indicia therealong providing an indication of an insertion depth for said first and second members based on a location of said at least one stop member relative thereto.

33. The instrument of claim 32, wherein said indicia are viewable through a window in said handle member.

34. An instrument for separating adjacent vertebrae, comprising:
a first member including at least a portion positionable along an endplate of one of the adjacent vertebrae;
a second member including at least a portion positionable along an endplate of the other of the adjacent vertebrae, said second member being movable relative to said first member and wherein at least one of said first and second members is structured to engage with and guide a cutting instrument along an outer surface thereof;
a handle assembly extending proximally from said first and second members; and
at least one actuating member positioned between said first and second members, said at least one actuating member being movable with said handle assembly from a first position wherein said first and second members include an unexpanded configuration relative to one another for insertion in the space between adjacent vertebrae to a second position providing an expanded configuration wherein said actuating member contacts at least one of said first and second members along at least a portion thereof contactable with the adjacent vertebral endplate thereby moving the at least one of said first and second members away from the other of said first and second members, wherein:
   at least one of said first and second members includes a central keyway opening along the outer surface thereof adapted to receive a guiding fin of the cutting instrument movable therealong;
   said at least one of said first and second members includes opposite sidewalls adapted to receiving guide portions of corner blades of the cutting instrument movable therealong; and
   said opposite sidewalls are beveled from the outer surface of said at least one of said first and second members toward a central axis of said at least one of said first and second members, and said at least one of said first and second members includes a support member adjacent an inner surface thereof extending along at least a portion of each of said sidewalls.

35. The instrument of claim 34, wherein said actuating member includes a wedge-shaped body movable along a cam surface of the at least one of the first and second members.

36. The instrument of claim 35, wherein each of said first and second members includes a cam surface facing one another and said wedge-shaped body is movable along each of said cam surfaces.

37. The instrument of claim 34, wherein said actuating member is coupled with said handle assembly and movable along a longitudinal axis of the instrument.

38. The instrument of claim 34, wherein said actuating member is recessed between said first and second members when said first and second members are in said unexpanded configuration.

39. An instrument for separating adjacent vertebrae, comprising:
   a first member including at least a portion positionable along an endplate of one of the adjacent vertebrae, said first member including a first width between opposite lateral sidewalls thereof;
   a second member including at least a portion positionable along an endplate of the other of the adjacent vertebrae, said second member including a second width between opposite lateral sidewalls thereof, said second member being movable relative to said first member and wherein at least one of said first member and said second member includes an instrument guide positioned between the lateral sidewalls thereof, said instrument guide being formed in an outer surface thereof and extending along a longitudinal axis of said at least one member;
   a handle assembly extending proximally from said first and second members; and
   at least one actuating member positioned between said first and second members and confined between said opposite lateral sidewalls of each of said first and second members, said at least one actuating member being movable from a first position wherein said first and second members include an unexpanded configuration relative to one another for insertion in the space between adjacent vertebrae to a second position providing an expanded configuration wherein said actuating member is moved relative to at least one of said first and second members to move the at least one of said first and second members away from the other of said first and second members, wherein:
   said instrument guide is a central keyway opening along the outer surface of said at least one of said first member and said second member, said keyway adapted to receive a guiding fin of a cutting instrument;
   said lateral sidewalls of said at least one of said first and second members are adapted to receive guide portions of corner blades of the cutting instrument; and
   said lateral sidewalls are beveled from the outer surface of said at least one of said first and second members toward a central axis of said at least one of said first and second members, and said at least one of said first and second members includes a support member adjacent an inner surface thereof extending along at least a portion of each of said sidewalls.

40. The instrument of claim 39, wherein said opposite lateral sidewalls of said first and second members are each beveled along an outer surface thereof to guide a cutting instrument therealong.

41. The instrument of claim 39, wherein each of said opposite lateral sidewalls of each of said first and second members includes an inner surface and said actuating member is confined between said inner surfaces.

42. The instrument of claim 39, wherein said actuating member includes at least one engagement member slidably engageable with a slot in one of said first and second members, said engagement member confining said actuating member between said opposite lateral sidewalls of said first and second members.

43. The instrument of claim 39, wherein said instrument guide is configured to slidably engage with a cutting instrument to guide the cutting instrument along said at least one of said first member and said second member.

44. An instrument for separating adjacent vertebrae, comprising:
   a first member including at least a portion positionable along an endplate of one of the adjacent vertebrae, said first member including a first width between opposite lateral sidewalls thereof;
   a second member including at least a portion positionable along an endplate of the other of the adjacent vertebrae, said second member including a second width between opposite lateral sidewalls thereof, said second member being movable relative to said first member and wherein at least one of said first member and said second member includes an instrument guide positioned between the lateral sidewalls thereof, said instrument guide being formed in an outer surface thereof and extending along a longitudinal axis of said at least one member;
   a handle assembly extending proximally from said first and second members; and at least one actuating member positioned between said first and second members and confined between said opposite lateral sidewalls of each of said first and second members, said at least one actuating member being movable from a first position wherein said first and second members include an unexpanded configuration relative to one another for insertion in the space between adjacent vertebrae to a second position providing an expanded configuration wherein said actuating member is moved relative to at least one of said first and second members to move the at least one of said first and second members away from the other of said first and second members, wherein said lateral sidewalls of said at least one of said first and second members are adapted to receive guide portions of corner blades of a cutting instrument and said lateral sidewalls are beveled from the outer surface of said at least one of said first and second members toward a central axis of said at least one of said first and second members, and said at least one of said first and second members includes a support member adjacent an inner surface thereof extending along at least a portion of each of said sidewalls.

* * * * *